United States Patent
Zhang et al.

(10) Patent No.: US 10,995,099 B2
(45) Date of Patent: May 4, 2021

(54) COMPOUNDS AND THEIR USES AS ACC INHIBITORS

(71) Applicant: NANJING RUIJIE PHARMATECH CO., LTD., Nanjing (CN)

(72) Inventors: Junbo Zhang, Nanjing (CN); Hong Liao, Nanjing (CN); Peipei Wang, Nanjing (CN); Peng Wang, Nanjing (CN)

(73) Assignee: Nanjing Ruijie Pharmatech Co., Ltd., Nanjing (CN)

( * ) Notice: Subject to any disclaimer, the term of this patent is extended or adjusted under 35 U.S.C. 154(b) by 0 days.

(21) Appl. No.: 16/631,800

(22) PCT Filed: Jul. 17, 2018

(86) PCT No.: PCT/CN2018/095973
§ 371 (c)(1),
(2) Date: Jan. 16, 2020

(87) PCT Pub. No.: WO2019/015583
PCT Pub. Date: Jan. 24, 2019

(65) Prior Publication Data
US 2020/0140454 A1    May 7, 2020

Related U.S. Application Data

(63) Continuation-in-part of application No. PCT/CN2017/093106, filed on Jul. 17, 2017.

(51) Int. Cl.
| | | |
|---|---|---|
| *C07D 495/04* | (2006.01) | |
| *A61P 1/16* | (2006.01) | |
| *C07D 405/12* | (2006.01) | |
| *C07D 413/10* | (2006.01) | |
| *C07D 413/14* | (2006.01) | |

(52) U.S. Cl.
CPC .............. *C07D 495/04* (2013.01); *A61P 1/16* (2018.01); *C07D 405/12* (2013.01); *C07D 413/10* (2013.01); *C07D 413/14* (2013.01)

(58) Field of Classification Search
CPC .................................. C07D 495/04; A61P 1/16
See application file for complete search history.

(56) References Cited

U.S. PATENT DOCUMENTS

| | | | | |
|---|---|---|---|---|
| 8,969,557 B2 * | 3/2015 | Harriman | ................ | A61P 35/00 |
| | | | | 544/278 |
| 9,453,026 B2 * | 9/2016 | Harriman | ............. | A61K 31/519 |
| 9,944,655 B2 * | 4/2018 | Harriman | .................. | A61P 3/00 |
| 10,472,374 B2 * | 11/2019 | Bhat | ...................... | A01N 43/90 |

FOREIGN PATENT DOCUMENTS

| | | |
|---|---|---|
| WO | 2017/091600 A1 | 6/2017 |
| WO | 2017/091617 A1 | 6/2017 |

OTHER PUBLICATIONS

Pouliot et al (2015): STN International HCAPLUS database, (Columbus, Ohio), Accession No. 2015: 254804.*

* cited by examiner

*Primary Examiner* — Golam M Shameem
(74) *Attorney, Agent, or Firm* — Weisun Rao; Venture Partner, LLC

(57) ABSTRACT

The present invention provides compounds of Formula (I) which can be used as ACC inhibitors and potently as therapeutic agents against diseases mediated by ACC.

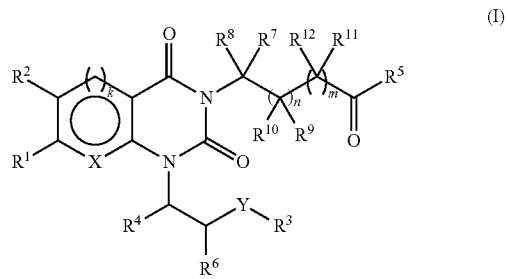

29 Claims, No Drawings

COMPOUNDS AND THEIR USES AS ACC INHIBITORS

CROSS-REFERENCE TO RELATED APPLICATION

This application claims priority to international application number PCT/CN2017/093106, filed on Jul. 17, 2017, the contents of which are incorporated herein by reference in their entirety.

BACKGROUND OF THE INVENTION

ACC is a multi-subunit enzyme in most prokaryotes and in the chloroplasts of most plants and algae, whereas it is a large, multi-domain enzyme in the endoplasmic reticulum of most eukaryotes. The most important function of ACC is to provide the malonyl-CoA substrate for the biosynthesis of fatty acids. The activity of ACC can be controlled at the transcriptional level as well as by small molecule modulators and covalent modification. The human genome contains the genes for two different ACCs—ACACA and ACACB. Uncontrolled ACC activities can lead to serious disease such as a metabolic disease (e.g., obesity), a liver disease (e.g., a nonalcoholic fatty liverdisease), or cancer.

Fatty acid metabolism dysregulated through elevated fatty acid synthesis (FASyn), impaired fatty acid oxidation (FAOxn), or both is a hallmark of various metabolic disorders, including insulin resistance, hepatic steatosis, dyslipidemia, obesity, metabolic syndrome (MetSyn), and nonalcoholic fatty liver disease (NAFLD), that can lead to the development of type 2 diabetes (T2DM), nonalcoholic steatohepatitis (NASH), and atherosclerotic vascular disease. Altered fatty acid metabolism also is a hallmark of cancer and contributes to the abnormal and sustained cellular proliferation of malignancy. Therefore inhibition of FASyn and/or stimulation of FAOxn have the potential to affect these maladies favorably. As a result of its unique position in intermediary metabolism, pharmacologic inhibition of acetyl-CoA carboxylase (ACC) offers an attractive modality for limiting FASyn in lipogenic tissues while simultaneously stimulating FAOxn in oxidative tissues. ACC catalyzes the ATP-dependent carboxylation of acetyl-CoA to form malonyl-CoA, the rate-limiting and first committed reaction in FASyn. This conversion proceeds in two half-reactions, a biotin carboxylase (BC) reaction and a carboxyltransferase (CT) reaction. ACC activity is tightly regulated through a variety of dietary, hormonal, and other physiological responses including feed-forward activation by citrate, feed-back inhibition by long-chain fatty acids, reversible phosphorylation and inactivation by AMP-activated protein kinase (AMPK), and modulation of enzyme production through altered gene expression. ACC exists as two tissue-specific isozymes that are encoded by separate genes and display distinct cellular distributions. ACC1 is a cytosolic enzyme present in lipogenic tissues (liver, adipose); ACC2 is a mitochondrially associated isozyme present in oxidative tissues (liver, heart, skeletal muscle). In the liver, malonyl-CoA formed in the cytoplasm by ACC1 is used primarily for FASyn and elongation, whereas malonyl-CoA formed at the mitochondrial surface by ACC2 acts primarily to regulate mitochondrial FAOxn through allosteric inhibition of carnitine palmitoyltransferase-1. This functional compartmentalization results from a combination of synthesis proximity and the rapid action of malonyl-CoA decarboxylase. In the heart and skeletal muscle, which lack ACC1 and thus have a limited capacity for FASyn, the malonyl-CoA formed by ACC2 functions primarily to regulate FAOxn. Adipose tissue primarily contains ACC1 to support FASyn in that tissue.

Obesity is a health crisis of epic proportions. The health burden of obesity, measured by quality-adjusted life-years lost per adult, has surpassed that of smoking to become the most serious, preventable cause of death. In the US, about 34% of adults have obesity, up from 31% in 1999 and about 15% in the years 1960 through 1980. Obesity increases the rate of mortality from all causes for both men and women at all ages and in all racial and ethnic groups. Obesity also leads to social stigmatization and discrimination, which decreases quality of life dramatically. The chronic diseases that result from obesity cost the US economy more than $150 billion in weight-related medical bills each year. Furthermore, about half of the obese population, and 25% of the general population, have metabolic syndrome, a condition associated with abdominal obesity, hypertension, increased plasma triglycerides, decreased HDL cholesterol, and insulin resistance, which increases the risk for type-2 diabetes (T2DM), stroke and coronary heart disease. [Harwood, Expert Opin. Ther. Targets 9: 267, 2005].

Diet and exercise, even when used in conjunction with the current pharmacotherapy, do not provide sustainable weight loss needed for long-term health benefit. Currently, only a few anti-obesity drugs are approved in the US, the fat absorption inhibitor orlistat (Xenical®), the 5-HT2C antagonist lorcaserin (Belviq®), and the combination therapy phentermine/topiramate) (Qsymia®). Unfortunately, poor efficacy and unappealing gastrointestinal side effects limit the use of orlistat. Surgery can be effective but is limited to patients with extremely high body-bass indices (BMI) and the low throughput of surgery limits the impact of this modality to about 200 k patients per year. The majority of obesity drugs in clinical development are designed to reduce caloric intake through central action in the CNS (e.g., anorectics and satiety agents). However, the FDA has taken an unfavorable position against CNS-active agents, due to their modest efficacy and observed/potential side-effect profiles.

The continuing and increasing problem of obesity, and the current lack of safe and effective drugs for treating it, highlight the overwhelming need for new drugs to treat this condition and its underlying causes, particularly related to ACC.

BRIEF SUMMARY OF THE INVENTION

In one aspect, the present invention provides a compound of Formula (I) or a pharmaceutically acceptable salt of an enantiomer thereof,

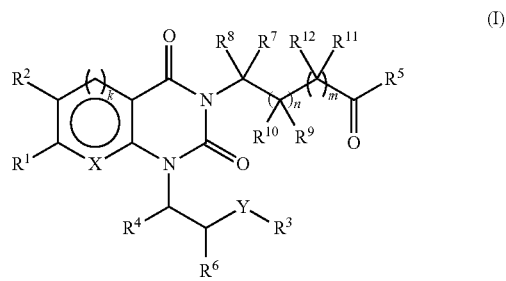

wherein
each of m, n, and k independently is 0, 1, or 2;
$R^1$ is H, halo, alkyl, haloalkyl, CN, amido, aryl, or heteroaryl, R² is H, alkyl, haloalkyl, CN, hydroxyl, or alkoxy;

R³ is H, alkyl, aryl, heteroaryl, cycloalkyl, or heterocycloalkyl, and is optionally substituted with halo, alkyl, or haloalkyl;

R⁴ is H, alkyl, haloalkyl, CN, hydroxyl, or alkoxy;

R⁵ is OR or N(R)₂;

R⁶ is aryl or heteroaryl and is optionally substituted with halo, alkyl, haloalkyl, CN, hydroxyl, or alkoxy;

each of R⁷ and R⁸ independently is H, alkyl, haloalkyl, alkoxy, or haloalkoxy; or alternatively, R⁷ and R⁸, together with the carbon atom to which they are bonded, form a 3- to 6-membered cycloalkyl which optionally contains one or two ring hetero groups each independently being O or NR';

each of R⁹, R¹⁰ R¹¹, and R¹², independently, is H, alkyl, haloalkyl, alkoxy, or haloalkoxy; or alternatively, R⁹ and R⁸, together with the carbon atoms to which they are bonded, form a 3- to 7-membered cycloalkyl which optionally contains one or two ring hetero groups each independently being O or NR'; or still alternatively, R⁷ and R¹⁰ together (not including the carbon atoms to which they are bonded) form a $C_{1-3}$ alkylene group, and R⁸ and R⁹ together (not including the carbon atoms to which they are bonded) form another $C_{1-3}$ alkylene group;

X is C(R)₂, S, O, or NR';

Y is S, O, or NR';

each R independently is H, alkyl, halo, or haloalkyl; and each of R' independently is H, halo, alkyl, haloalkyl, CN, or hydroxyl.

In some embodiments, k is 0.

In some embodiments, X is S or O (e.g., S).

In some embodiments, k is 1.

In some embodiments, X is CH₂, S, O, or NH (e.g., CH₂).

In some embodiments, Y is S, O or NH (e.g., O).

In some embodiments, R¹ is halo, haloalkyl, CN, or heteraryl. For example, R¹ is Br, F, CF₃, CN, oxazolyl, oxazolyl, or oxadiazolyl. For some other example, R¹ is Br, F, CF₃, CN, 2-oxazolyl, 4-oxazolyl, or 4-oxadiazolyl, or 5-oxadiazolyl.

In some embodiments, each of R² and R⁴ independently is H or alkyl.

In some embodiments, R³ is cycloalkyl or heterocycloalkyl and is optionally substituted with halo, alkyl, or haloalkyl. In some examples, R³ is heterocycloalkyl optionally substituted with halo, alkyl, or haloalkyl. Specific examples include but are not limited to tetrahydro-2H-pyranyl, tetrahydrofuranyl, tetrahydro-2H-thiopyranyl, and tetrahydrothiophenyl, which are optionally substituted with halo, alkyl, or haloalkyl.

In some embodiments, R³ is 4-(tetrahydro-2H-pyranyl) or 3-(tetrahydrofuranyl).

In some embodiments, R⁵ is OR or N(R)₂, wherein each R is independently H or alkyl.

In some embodiments, R is H.

In some embodiments, R⁶ is phenyl, pyridinyl, pyrrolyl, orthiophenyl, and is optionally substituted with halo, alkyl, haloalkyl, CN, hydroxyl, or alkoxy. For example, R⁶ is phenyl substituted with halo, alkyl, haloalkyl, or alkoxy.

In some embodiments, m is 0 and n is 1.

In some embodiments, each of R⁷ and R⁸ independently is H, alkyl, haloalkyl, alkoxy, or haloalkoxy; and each of R⁹ and R¹⁰, independently, is H, alkyl, haloalkyl, alkoxy, or haloalkoxy.

In some embodiments, R⁷ and R⁸, together with the carbon atom to which they are bonded, form a 3- to 6-membered cycloalkyl which optionally contains one or two ring hetero groups each independently being O or NR'; and each of R⁹ and R¹⁰, independently, is H, alkyl, haloalkyl, alkoxy, or haloalkoxy.

In some embodiments, R⁷ and R⁸, together with the carbon atom to which they are bonded, form a 3- to 6-membered cycloalkyl which optionally contains one ring hetero group of O. Examples of such cycloalkyl with optional ring hetero groups include but are not limited to

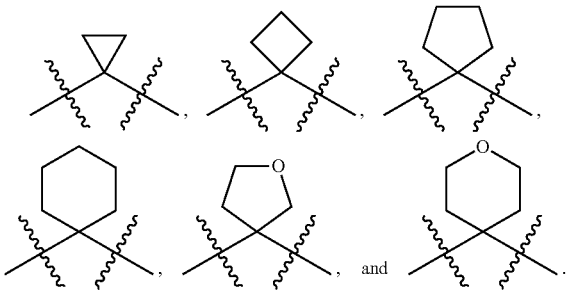

In some embodiments, each of R⁷ and R¹⁰, independently, is H, alkyl, haloalkyl, alkoxy, or haloalkoxy; and R⁸ and R⁹, together with the carbon atoms to which they are bonded, form a 3- to 7-membered cycloalkyl which optionally contains one or two ring hetero groups each independently being O or NR'.

In some embodiments, each of R⁷ and R¹⁰, independently, is H, alkyl, or haloalkyl; and R⁸ and R⁹, together with the carbon atoms to which they are bonded, form a 3- to 7-membered cycloalkyl.

In some embodiments, R⁷ and R¹⁰ together (not including the carbon atoms to which they are bonded) form a $C_{1-3}$ alkylene group, and R⁸ and R⁹ together (not including the carbon atoms to which they are bonded) form another $C_{1-3}$ alkylne group. For example, such an alkylene group can be a methylene or ethylene group.

In some embodiments, each R and each R' independently is H, halo, alkyl, or haloalkyl.

Specific examples of the compounds of this invention include:

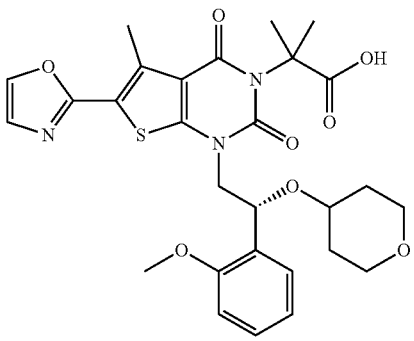

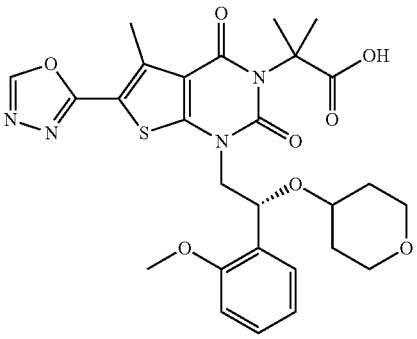

-continued
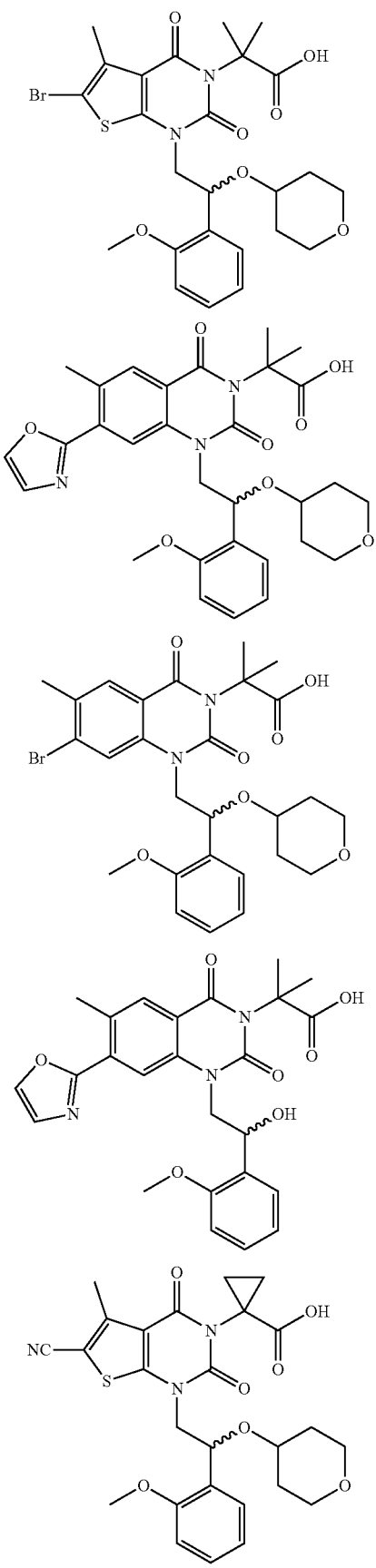
-continued
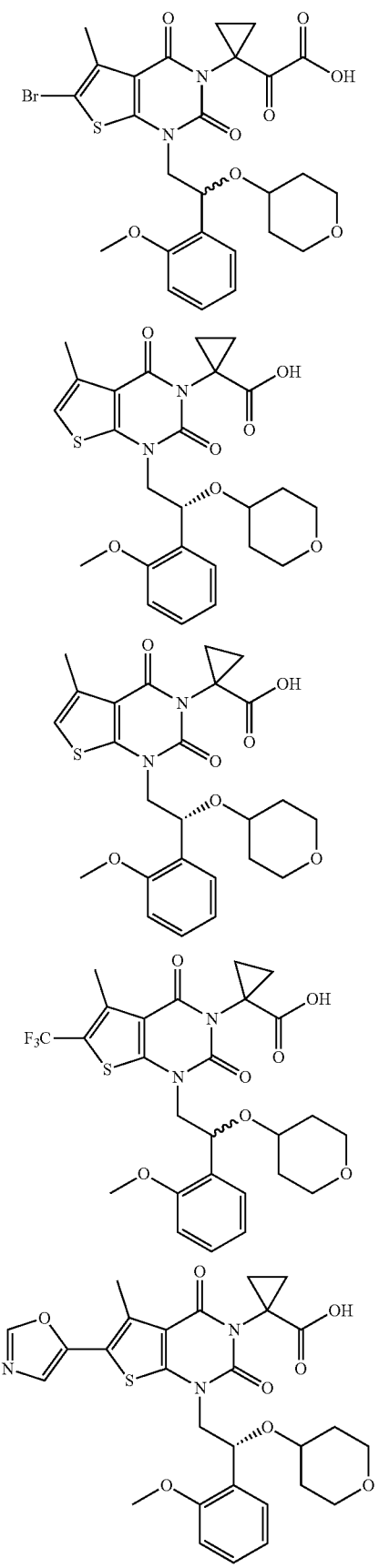

-continued
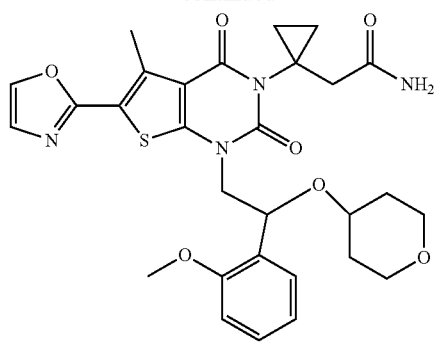
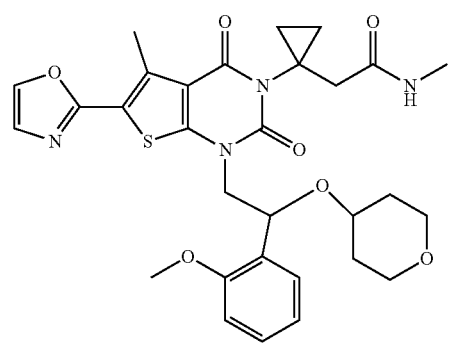
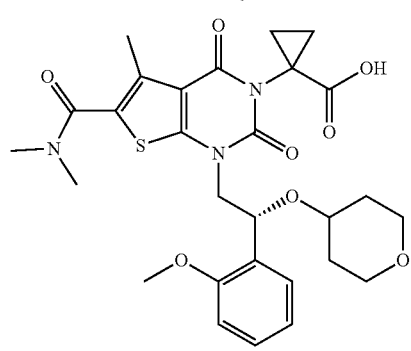
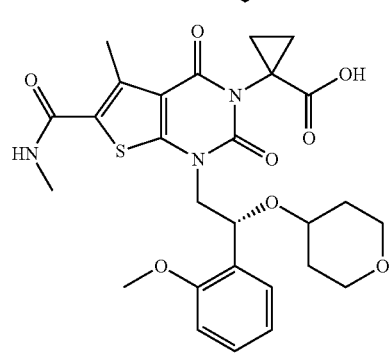
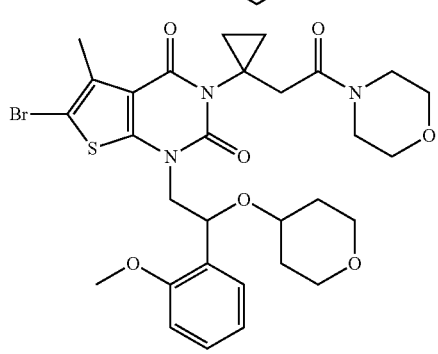
-continued
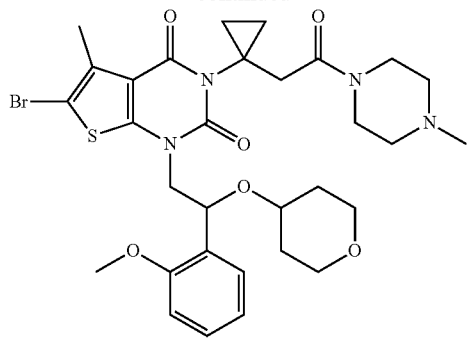
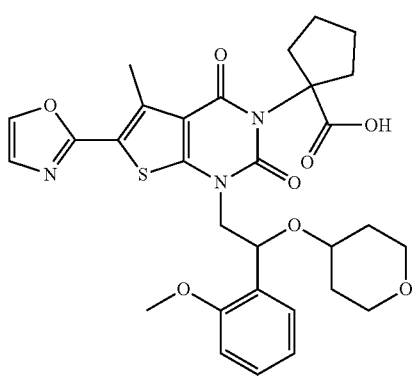
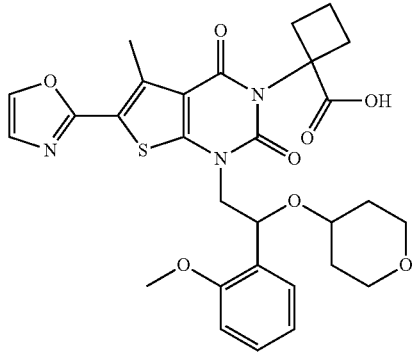
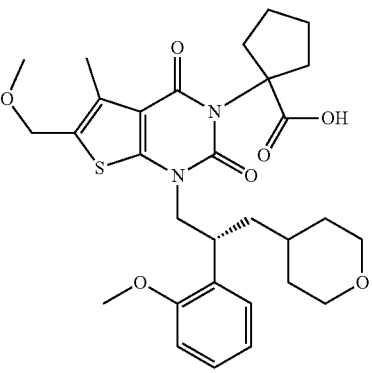

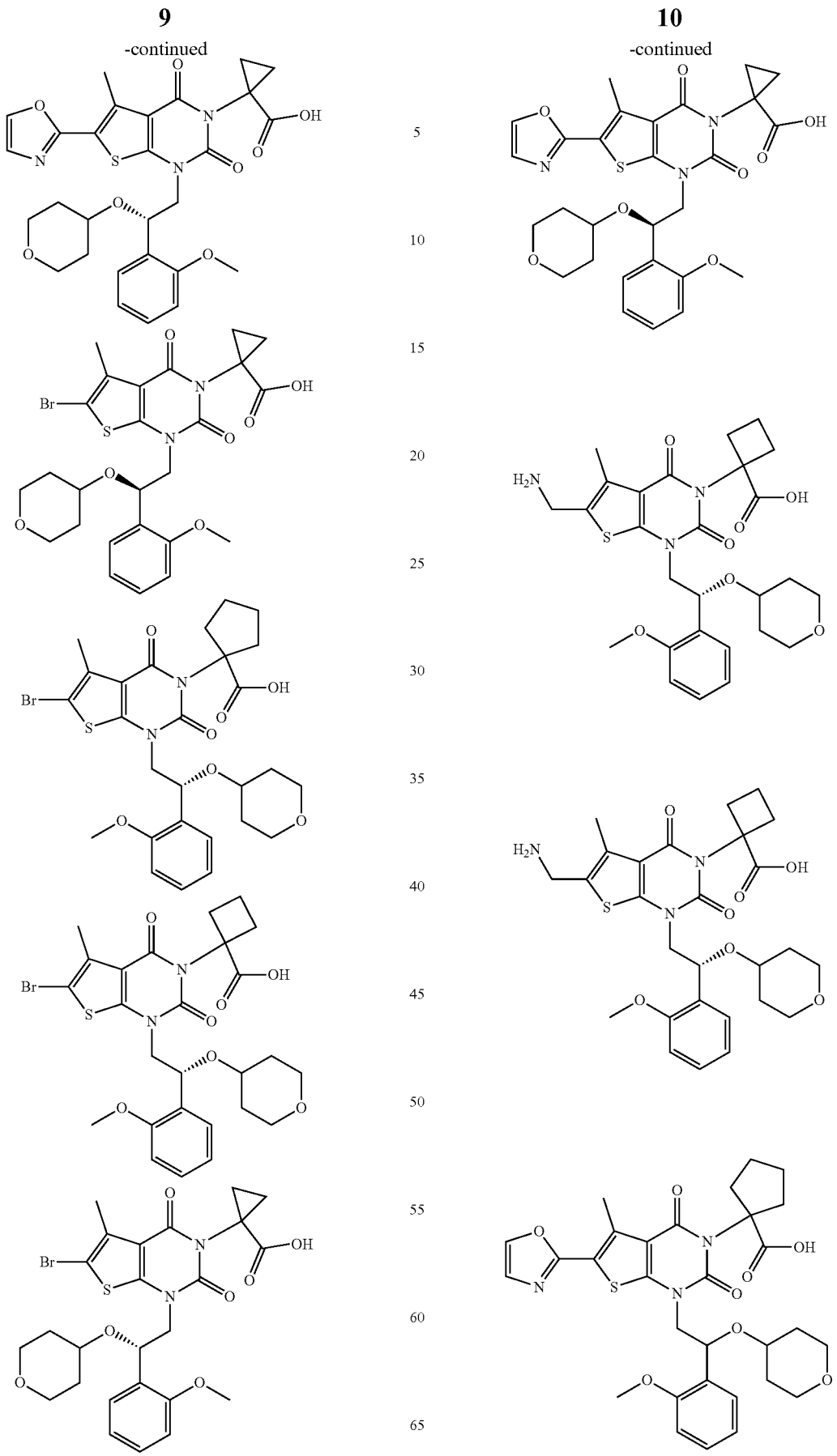

-continued
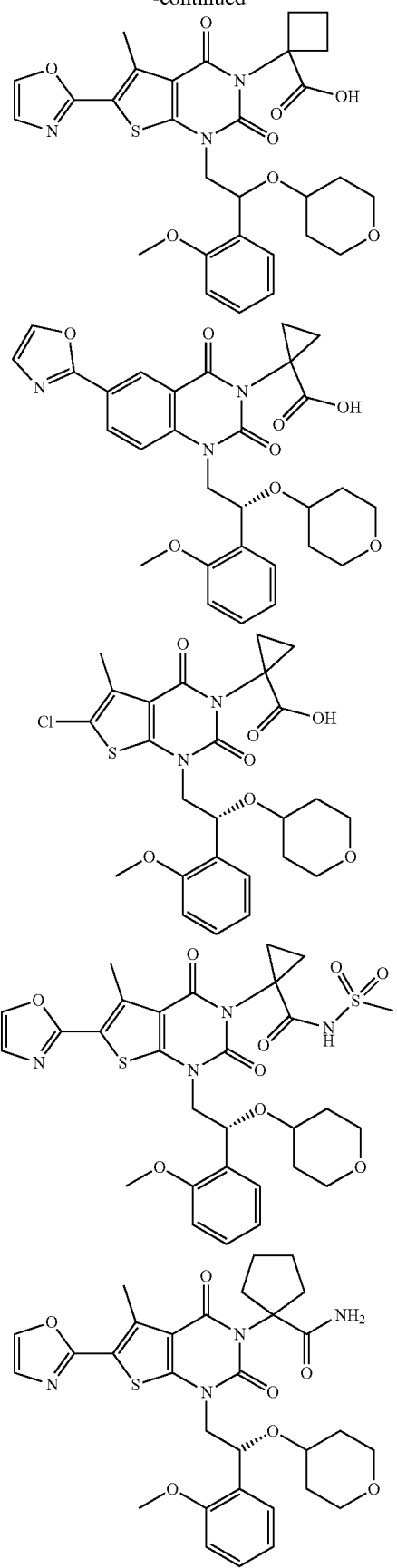
-continued
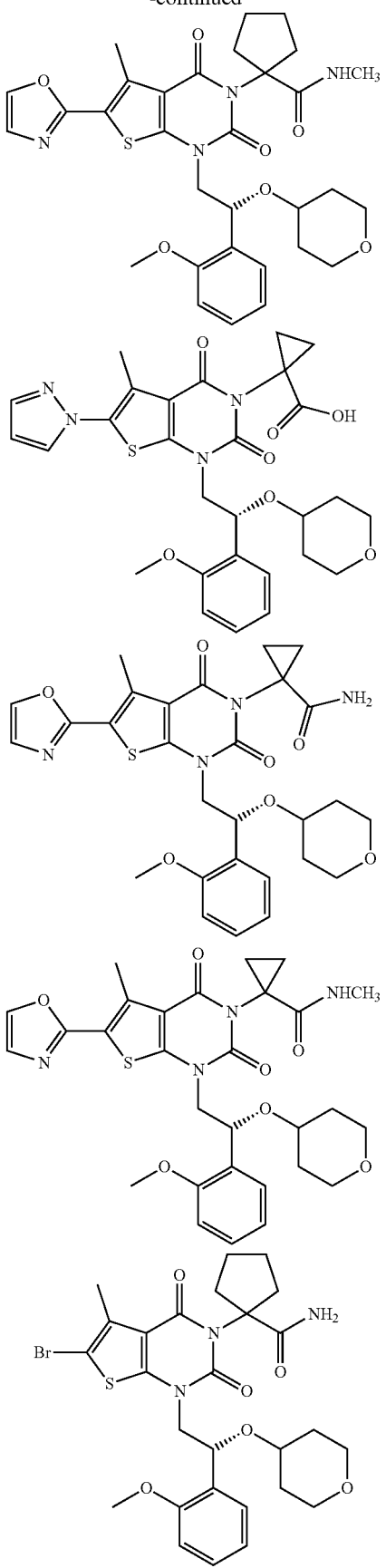

-continued
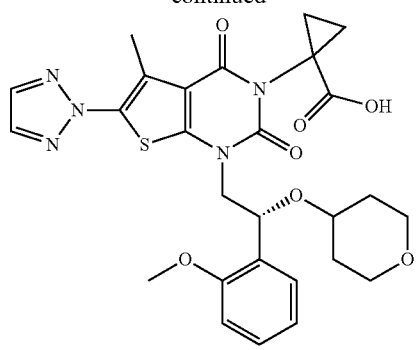
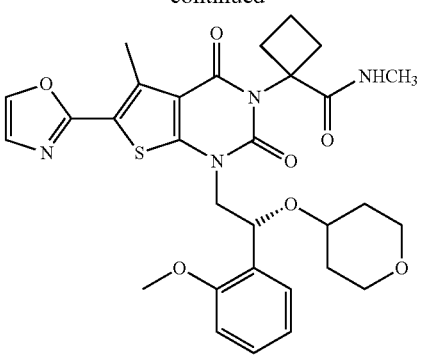
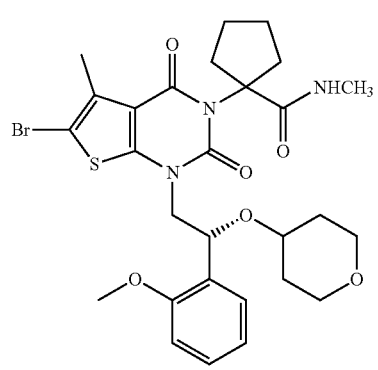
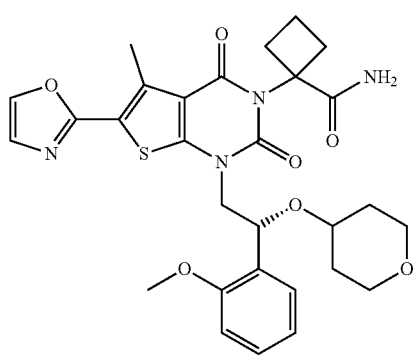
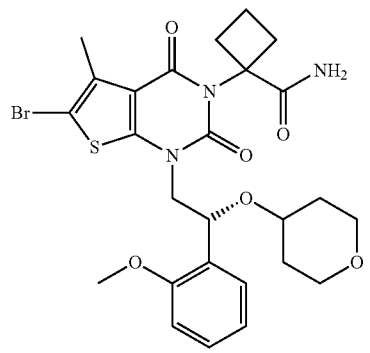
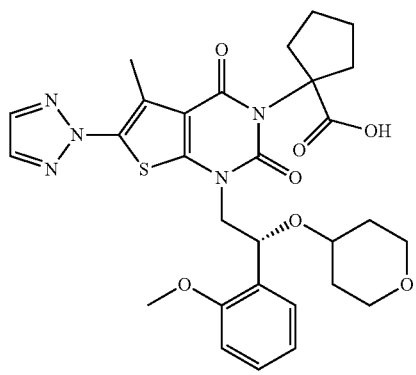
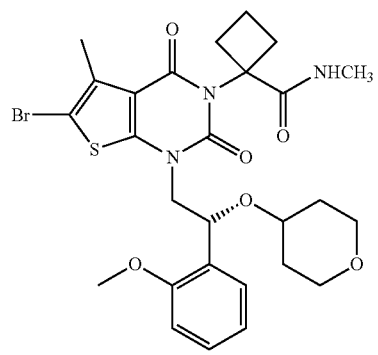
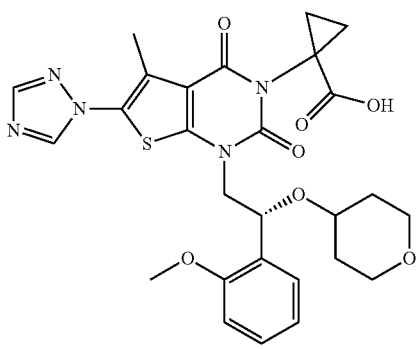

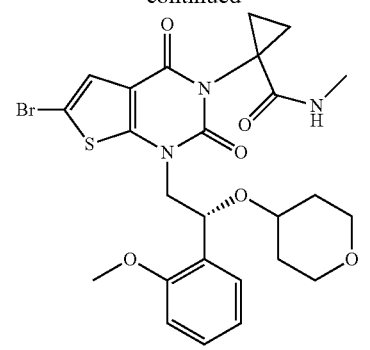
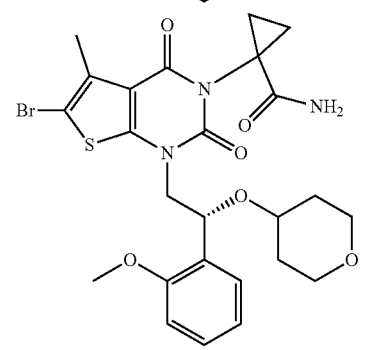
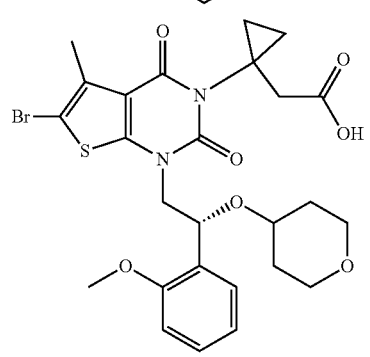
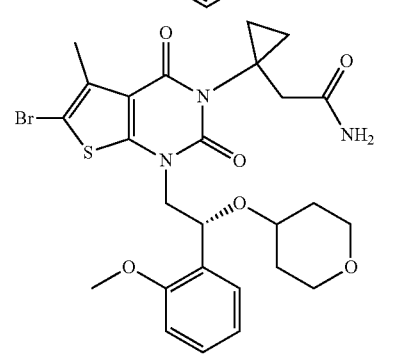
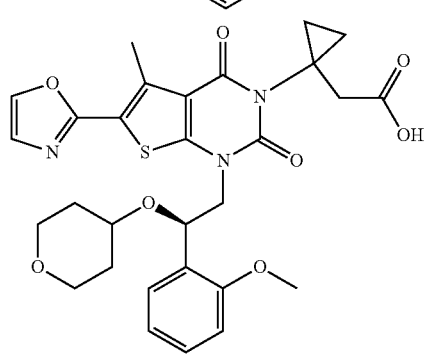
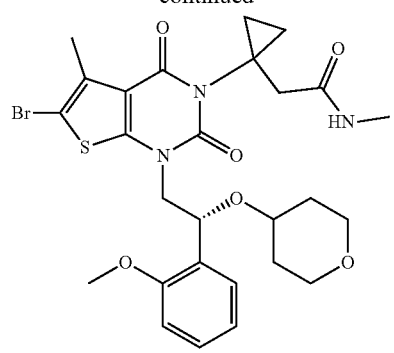
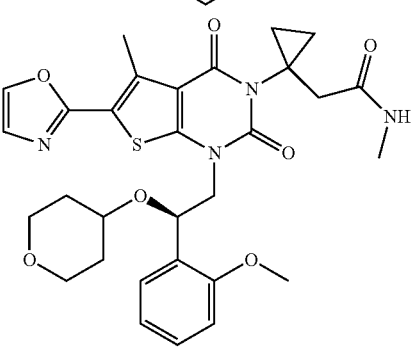
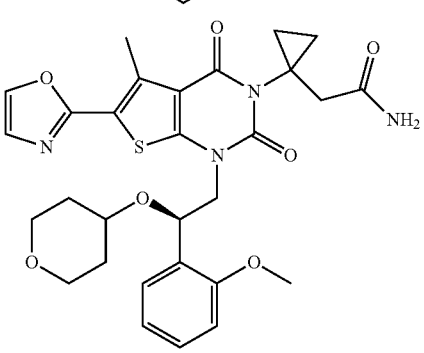
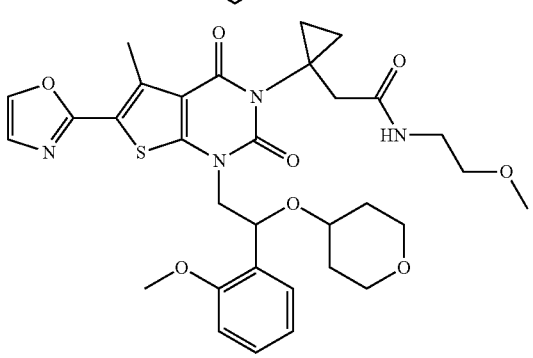
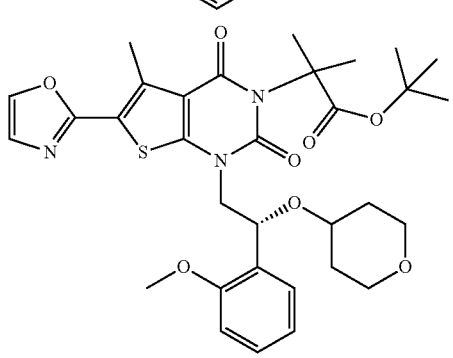

17
-continued
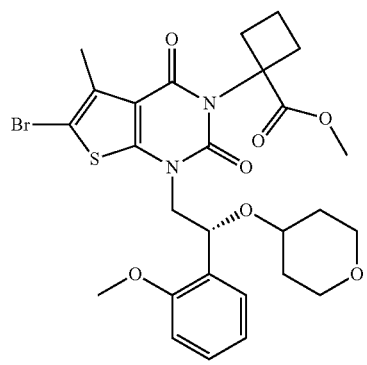
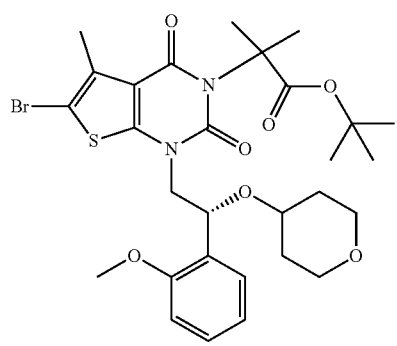
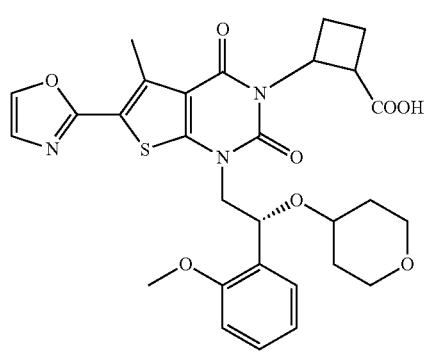
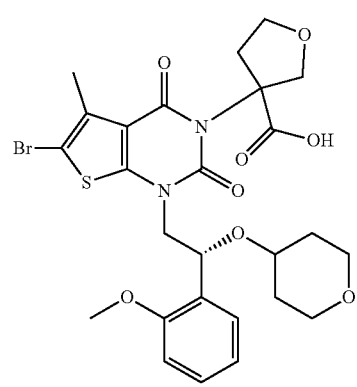
18
-continued
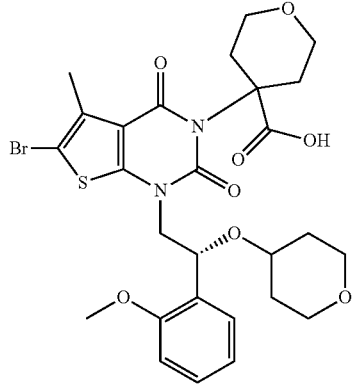
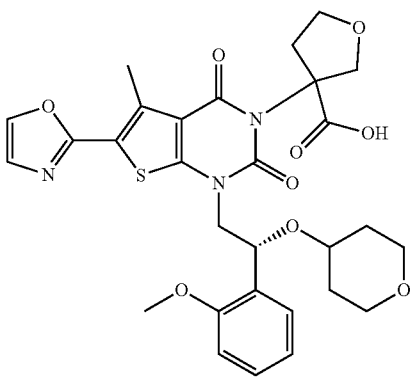
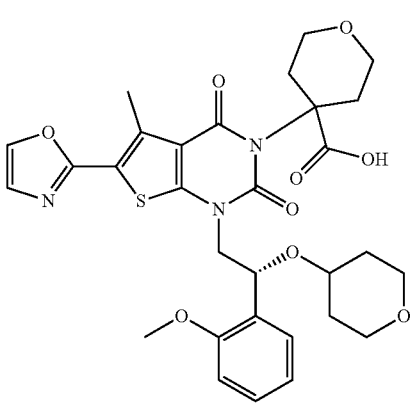
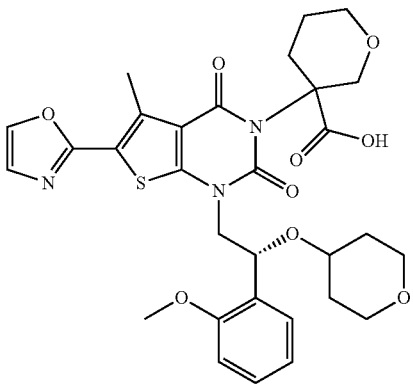

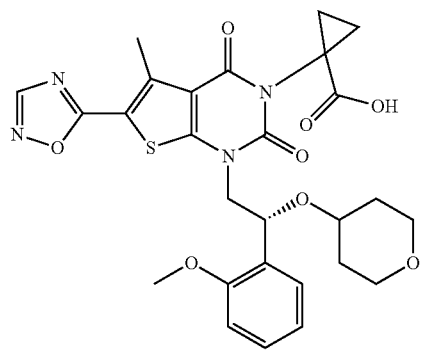
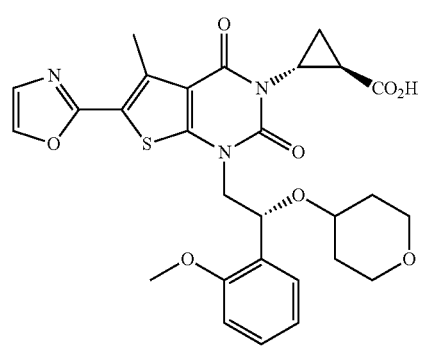
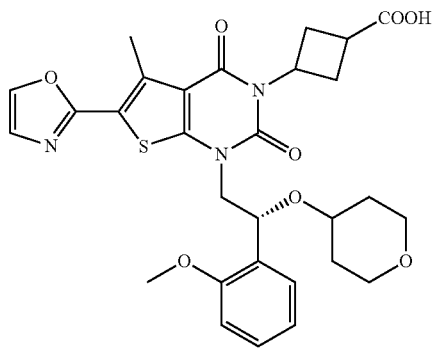
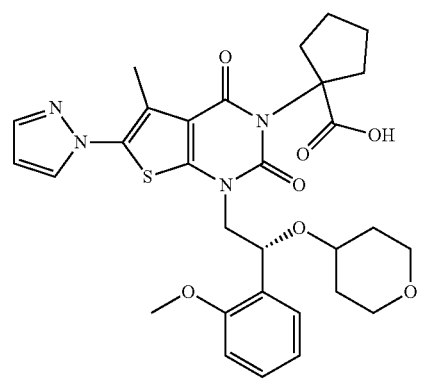
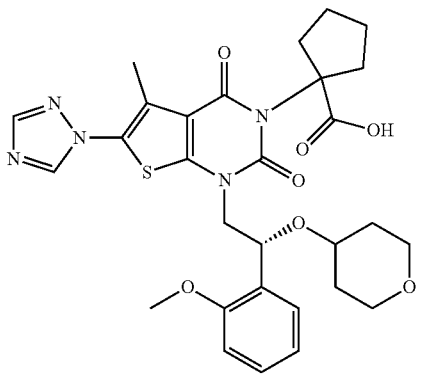
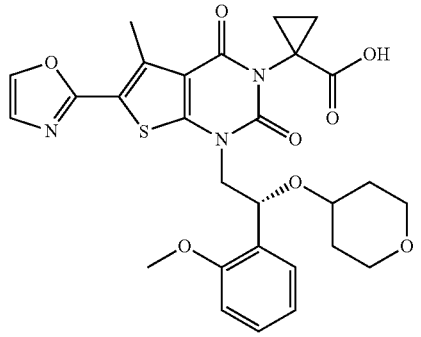
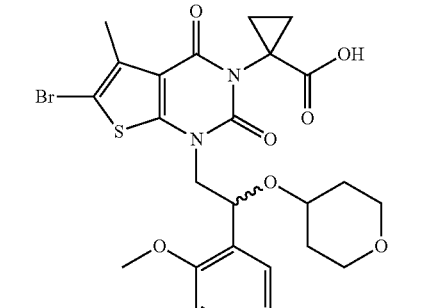
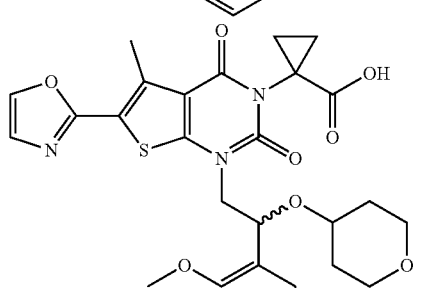
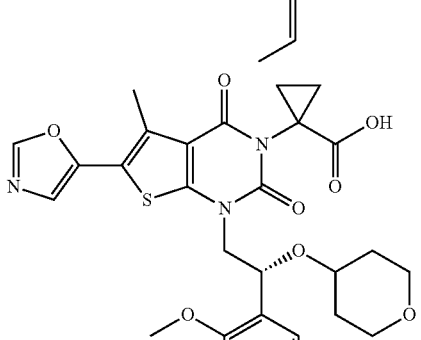

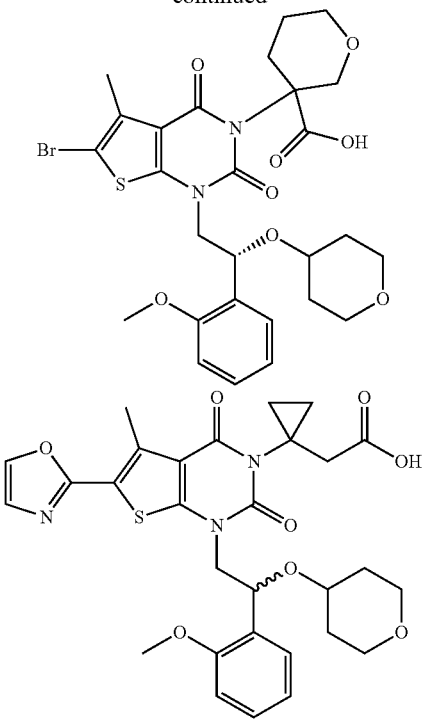

Another aspect of the invention provides pharmaceutical compositions each comprising a therapeutically effective amount of any of the compounds described above and a pharmaceutically acceptable carrier.

Still another aspect of the invention provides methods for inhibiting ACC in a subject in need thereof, and the methods include administering to the subject any of the compounds or the pharmaceutical compositions described above.

Yet still another aspect of this invention provides methods for treating a nonalcoholic fatty liver disease, a metabolic disease or cancer in a subject in need therefore. Such methods include administering to the subject a therapeutically effective amount of any of the compounds or the pharmaceutical compositions described above.

Examples of the nonalcoholic fatty liver disease include but are not limited to nonalcoholic steatohepatitis, hepatic steatosis, macrovesicular steatosis, advanced fibrosis, and cirrhosis.

Examples of the metabolic disorder include but are not limited to obesity, dyslipidemia and hyperlipidemia. The obesity can be a symptom of Prader-Willi syndrome, Bardet-Biedl syndrome, Cohen syndrome, or MOMO syndrome; or the obesity can be a side effect of the administration of a medication selected from the group selecting from insulin, sulfonylureas, thiazolidinediones, antipsychotics, antidepressants, steroids, anticonvulsants (including phenyloin and valproate), pizotifen, and hormonal contraceptives.

Examples of the cancer include but are not limited to liver cancer, melanoma, liposarcoma, lung cancer, breast cancer, prostate cancer, leukemia, kidney cancer, esophageal cancer, brain cancer, lymphoma or colon cancer.

DETAILED DESCRIPTION OF THE INVENTION

Definitions

The compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "alkyl" refers to a singly-radicalized (i.e., having one radical for forming one covalent bond) straight or branched hydrocarbon group represented by —CnH2n+1 in which n can be an integer of 1 to 18, 1 to 12, 1 to 8, 1 to 6, or 1 to 4. The term "lower alkyl" refers to a C1-4 straight or branched alkyl group. Exemplary lower alkyl groups are methyl, ethyl, propyl, isopropyl, butyl, isobutyl, and tert-butyl.

The term "lower haloalkyl" refers to a C1-4 straight or branched alkyl group that is substituted with one or more halogen atoms.

The term "alkylene" refers to a doubly-radicalized (i.e., having two radicals for forming two covalent bonds) straight or branched hydrocarbon group represented by —CnH2n in which n can be an integer of 1 to 18, 1 to 12, 1 to 8, 1 to 6, or 1 to 4.

As is typically the case, the term "ene" as contained in "alkylene" or "phenylene", or "enyl" as in "cyclopropylenyl" or "cyclobutylenyl", means that the underlying group has two radicals that can be used to form two bonds.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent C1-8 (or C1-6) saturated or unsaturated, straight or branched, hydrocarbon chain", refers to bivalent alkylene, alkenylene, and alkynylene chains that are straight or branched as defined herein.

As used herein, the term "alkylene" refers to a bivalent alkyl group. An "alkylene chain" is a polymethylene group, i.e., —(CH2)n-, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As used herein, the term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the structure

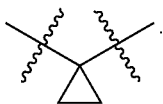 [SMILES: *C1(*)CC1]

As used herein, the term "cyclobutylenyl" refers to a bivalent cyclobutyl group of the following structure:

As used herein, the term "oxetanyl" refers to a bivalent oxetanyl group.

As used herein, the term "halogen" means F, Cl, Br, or I.

As used herein, the term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetra hydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetra hydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR$_2$; —N(R°)C(S)NR$_2$; —(CH$_2$)$_{0-4}$N(R°)C(O)OR°; —N(R°)N(R°)C(O)R°; —N(R°)N(R°)C(O)NR$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$C(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R°, -(haloR°), —(CH$_2$)$_{0-2}$OH, —(CH$_2$)$_{0-2}$OR°, —(CH$_2$)$_{0-2}$CH(OR°)$_2$; —O(haloR°), —CN, —N$_3$, —(CH$_2$)$_{0-2}$C(O)R°, —(CH$_2$)$_{0-2}$C(O)OH, —(CH$_2$)$_{0-2}$C(O)OR, —(CH$_2$)$_{0-2}$SR°, —(CH$_2$)$_{0-2}$SH, —(CH$_2$)$_{0-2}$NH$_2$, —(CH$_2$)$_{0-2}$NHR°, —(CH$_2$)$_{0-2}$NR°$_2$, —NO$_2$, —SiR°$_3$, —OSiR°$_3$, —C(O)SR°, —(C$_{1-4}$ straight or branched alkylene)C(O)OR°, or —SSR° wherein each R° is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5- to 6-membered saturated, partially unsaturated, or aryl ring having 0-4 heteroatoms each independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R°, -(haloR°), —OH, —OR°, —O(haloR°), —CN, —C(O)OH, —C(O)OR°, —NH$_2$, —NHR°, —NR°$_2$, or —NO$_2$, wherein each R° is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R°, -(haloR°), —OH, —OR°, —O(haloR°), —CN, —C(O)OH, —C(O)OR°, —NH$_2$, —NHR°, —NR°$_2$, or —NO$_2$, wherein each R° is unsubstituted or where preceded by "halo" is substituted only with one or more halogens, and is independently C$_{1-4}$ aliphatic, —CH$_2$Ph, —O(CH2)0-1Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+($C_{1-4}$alkyl)$_4$ salts. Representative alkali oralkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "enantiomer", also known as an optical isomer, refers to one of two stereoisomers that have at least a chiral atom (e.g., carbon atom in its R or S configuration) and are mirror images of each other and non-superposable (not identical), much as one's left and right hands are the same except for being reversed along one axis. A single chiral atom or similar structural feature in a compound causes that compound to have two possible structures which are non-superposable, each a mirror image of the other.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, or as probes in biological assays, or as therapeutic agents in accordance with the present invention. In certain embodiments, a warhead moiety, $R^1$, of a provided compound comprises one or more deuterium atoms.

Unless specifically specified otherwise, the scope of the term "H" (or hydrogen) includes all of its isotopic forms (e.g., $^1H$, $^2H$, and $^3H$), and the scope of the term "C" (or carbon) includes all of its isotopic forms (e.g., $^{12}C$, $^{13}C$, and $^{14}C$).

EXEMPLARY COMPOUNDS OF THE INVENTION

Example 1. Methyl-1-(6-bromo-5-methyl-2,4-dioxo-1H-thieno[2,3-d]pyrimidin-3-yl) cyclopropanecarboxylate This title compound was prepared according to the following reaction scheme:

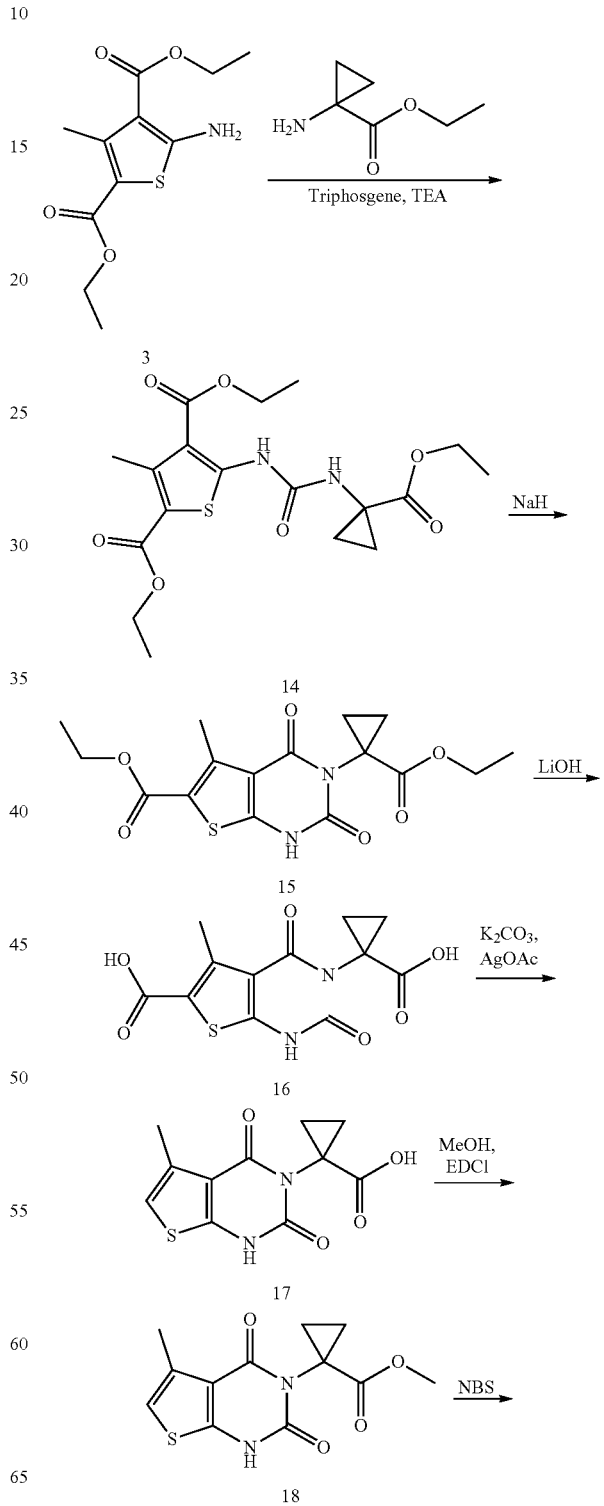

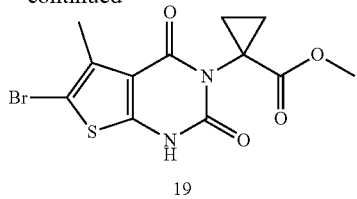

19

Synthesis of diethyl-5-[(1-ethoxycarbonylcyclopropyl)carbamoylamino]-3-methyl-thiophene-2,4-dicarboxylate (14)

Triphosgene (390.46 mg, 1.32 mmol) was added a solution of compound 3 (996.09 mg, 3.87 mmol) in DCM (6.00 mL) at 0° C. under N2. The mixture was added dropwise TEA (1.57 g, 15.48 mmol) and was stirred at 0° C. for 2 hr, ethyl 1-aminocyclopropanecarboxylate (500.00 mg, 3.87 mmol) was added. The mixture was stirred at 0° C. for overnight. The mixture reaction was added water and extracted with DCM, the organic layer was washed with brine, dried with Na2SO4 and concentrated. The crude was purified by column chromatography (P/E=8/1) to afford 14 (540.00 mg, 1.31 mmol, 33.83% yield). $^1$H NMR (400 MHz, CDCl$_3$): δ 4.34-4.26 (m, 4H), 4.18-4.16 (m, 2H), 2.74 (s, 3H), 1.40-1.30 (m, 9H), 1.23-1.21 (m, 4H).

Synthesis of ethyl-3-(1-ethoxycarbonylcyclopropyl)-5-methyl-2,4-dioxo-1H-thieno[2,3-d]pyrimidine-6-carboxylate (15)

To a solution of compound 4 (520.00 mg, 1.26 mmol) in 1,4-dioxane (8.00 mL), NaH (45.36 mg, 1.89 mmol) was added. The mixture was heated to reflux for 1 hr. The mixture reaction was quenched by saturated NH4Cl aqueous and extracted with EA, the organic layer was concentrated. The crude was purified by column chromatography (P/E=3/1) to afford 15 (210.00 mg, 573.16 umol, 45.49% yield) as a white solid. $^1$H NMR (400 MHz, CDCl$_3$): δ 4.37-4.31 (m, 2H), 4.22-4.16 (t, 2H), 2.81 (s, 3H), 1.41-1.34 (m, 6H), 1.25-1.16 (m, 4H).

Synthesis of 3-(1-carboxycyclopropyl)-5-methyl-2,4-dioxo-1H-thieno[2,3-d]pyrimidine-6-carboxylic Acid (16)

To a solution of compound 5 (8.30 g, 22.65 mmol) in H2O/THF (200.00 mL) was added LiOH (3.80 g, 158.55 mmol). The mixture reaction was heated to 80° C. overnight. The mixture reaction was acidified to PH 2 with 1M HCl and extracted with EA, the organic layer was dried and concentrated to afford compound 16 (6.70 g, 21.59 mmol, 95.34% yield) as a white solid. 1H NMR (400 MHz, DMSO): δ 13.00 (s, 2H), 12.38 (s, 1H), 2.70 (s, 3H), 1.72-1.61 (m, 2H), 1.35-1.26 (m, 2H).

Synthesis of 1-(5-methyl-2,4-dioxo-1H-thieno[2,3-d]pyrimidin-3-yl) cyclopropanecarboxylic acid A mixture of compound 6 (200.00 mg, 644.58 μmol), K$_2$CO$_3$ (1.61 mmol) and AgOAc (402.89 mg, 2.90 mmol) was dissolved in NMP (5.00 mL). The mixture reaction was heated to 110° C. for overnight. The reaction was added water and acidified to pH 2 with 1.0 M HCl. The mixture was extracted with EA, the organic phase dried and concentrated. The residue was purified by column chromatography (DCM/MeOH=10/1) to afford compound 17 (100.00 mg, 375.56 umol, 58.26% yield) as a yellow solid. $^1$H NMR (400 MHz, DMSO): δ 12.70 (s, 1H), 12.09 (s, 1H), 6.69 (s, 1H), 2.33 (s, 3H), 1.69-1.61 (m, 2H), 1.33-1.27 (m, 2H).

Synthesis of methyl-1-(5-methyl-2,4-dioxo-1H-thieno[2,3-d]pyrimidin-3-yl)cyclopropanecarboxylate (18)

A mixture of compound 7 (100.00 mg, 375.56 μmol) and MeOH (19.16 mg, 1.13 mmol) was dissolved in DCM (3.00 mL), DMAP (4.59 mg, 37.56 μmol) and EDCl (143.84 mg, 751.12 umol) was added. The mixture was stirred at rt for 3 hr. The mixture reaction was added water and extracted with DCM, the organic layer was dried and concentrated. The residue was purified by column chromatography (P/E=2/1) to afford compound 18(70.00 mg, 249.73 μmol, 66.50% yield) as a white solid. $^1$H NMR (400 MHz, CDCl3): δ 10.62 (s, 1H), 6.40 (s, 1H), 3.71 (s, 3H), 2.45 (s, 3H), 2.05-1.94 (m, 2H), 1.42 (m, 2H).

Synthesis of methyl-1-(6-bromo-5-methyl-2,4-dioxo-1H-thieno[2,3-d]pyrimidin-3-yl) cyclopropanecarboxylate (19)

To a solution of compound 8 (500.00 mg, 1.78 mmol) in DMF (10.00 mL) at −10° C., NBS (316.80 mg, 1.78 mmol) was added. The reaction mixture was stirred at −10° C. for 2 hr. The reaction mixture was added saturated NH4Cl aqueous and extracted with EA, the organic layer was washed with brine, dried and concentrated, The crude was purified by column chromatography (P/E=2/1) to afford compound 19 (500.00 mg, 1.39 mmol, 78.09% yield) as a white solid. $^1$H NMR (400 MHz, DMSO): δ 12.20 (s, 1H), 3.59 (s, 3H), 2.30 (s, 3H), 1.74-1.68 (m, 2H), 1.39-1.36 (m, 2H).

Example 2. Tert-butyl-2-[6-bromo-1-[2-(2-methoxyphenyl)-2-tetrahydropyran-4-yloxy-ethyl]-5-methyl-2,4-dioxo-thieno[2,3-d]pyrimidin-3-yl]-2-methylpropanoate (20), and tert-butyl-2-[6-bromo-2-[2-(2-methoxyphenyl)-2-tetrahydropyran-4-yloxy-ethoxy]-5-methyl-4-oxo-thieno[2,3-d]pyrimidin-3-yl]-2-methyl-propanoate (21)

A mixture of the title compounds was prepared according to the following reaction scheme:

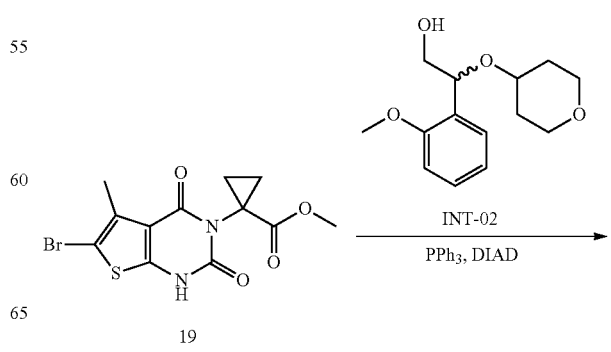

-continued

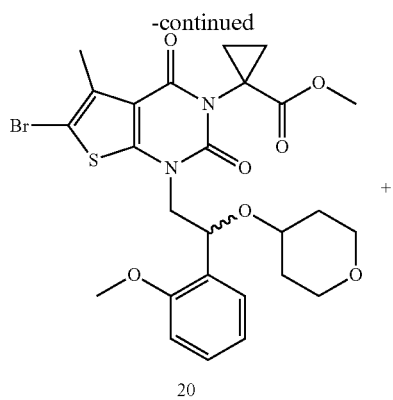
20

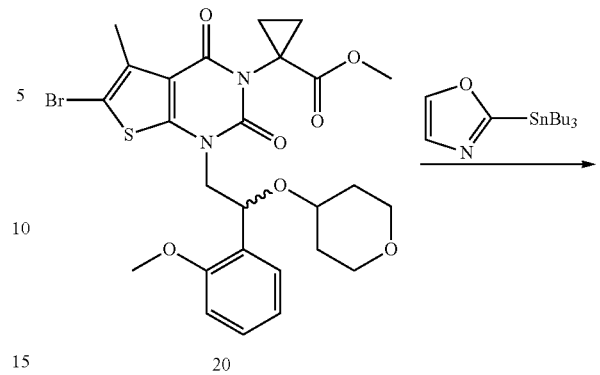
20

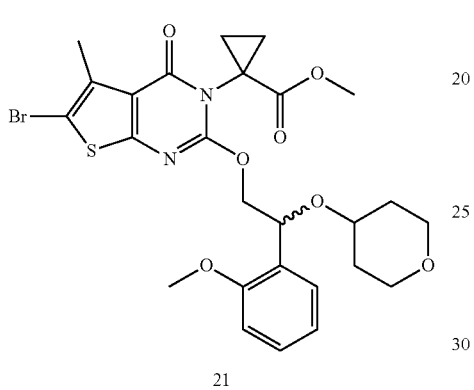
21

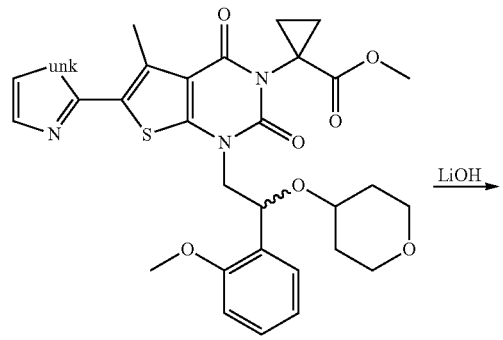
22

A 100 mL 3-necked round-bottom flask was charged with THF (8.00 mL), compound 19 (330.00 mg, 818.27 µmol), compound 10 (309.69 mg, 1.23 mmol) and PPh3 (643.87 mg, 2.45 mmol) under N$_2$, was added DIAD (237.52 mg, 1.80 mmol). The reaction was stirred at room temp for overnight. The reaction mixture was concentrated and the residue was purified by column chromatography (P/E=15/1) to compound 21 (240.00 mg, 376.42 µmol, 46.00% yield) and 20 (120.00 mg, 188.21 µmol, 23.00% yield) as a white solid.

Compound 20: $^1$H NMR (400 MHz, CDCl$_3$): δ 7.47 (m, 1H), 7.29-7.26 (m, 1H), 7.00-6.98 (m, 1H), 6.89-6.87 (m, 1H), 5.31-5.26 (m, 1H), 4.44-4.41 (m, 1H), 3.94-3.86 (m, 2H), 3.84 (s, 3H), 3.50-3.49 (m, 1H), 3.38-3.33 (m, 2H), 2.45 (s, 3H), 2.17-1.75 (m, 4H), 1.64-1.61 (m, 3H), 1.60-1.57 (m, 2H), 1.46-1.45 (m, 2H), 1.45-1.30 (m, 2H), 1.28-1.26 (m, 3H).

Compound 21: $^1$H NMR (400 MHz, CDCl$_3$): δ7.59-7.48 (t, 1H), 7.31-7.26 (m, 1H), 7.00 (m, 1H), 6.89-6.85 (d, 1H), 5.35 (m, 1H), 3.87-3.82 (s, 3H), 3.73-3.70 (m, 1H), 3.69-3.60 (m, 3H), 3.43-3.33 (m, 3H), 2.44 (s, 3H), 2.17 (s, 1H), 2.00-1.99 (m, 1H), 1.99-1.90 (m, 1H), 1.70 (s, 3H), 1.60-1.52 (m, 2H), 1.36-1.24 (m, 5H).

Example 3. 1-[1-[2-(2-methoxyphenyl)-2-tetrahydropyran-4-yloxy-ethyl]-5-methyl-6-oxazol-2-yl-2,4-dioxo-thieno[2,3-d]pyrimidin-3-yl]cyclopropanecarboxylic acid (16331-02)

This title compound was prepared according to the following reaction scheme:

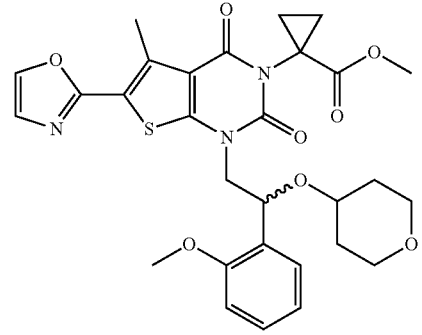
16331-02

Preparation of tert-butyl-2-[6-bromo-1-[2-(2-methoxyphenyl)-2-tetrahydropyran-4-yloxy-ethyl]-5-methyl-2,4-dioxo-thieno[2,3-d]pyrimidin-3-yl]-2-methyl-propanoate (22)

A mixture of compound 20 (160.00 mg, 250.95 umol) in toluene (10.00 mL) was added Pd(PPh3)4 (86.88 mg, 75.29 umol) under an atmosphere of nitrogen. The mixture was heated to reflux overnight and then concentrated. The residue was purified by preparative HPLC to afford compound 22 (36.00 mg, 94.11 mol, 37.50% yield) as a yellow solid. 1H NMR (400 MHz, CDCl$_3$): δ 7.73 (s, 1H), 7.60-7.50 (m, 1H), 7.33-7.29 (m, 1H), 7.26 (s, 1H), 7.04-7.00 (m, 1H), 6.90-6.88 (m, 1H), 5.43-5.42 (m, 1H), 3.90-3.86 (m, 3H), 3.71-3.68 (m, 2H), 3.43-3.41 (m, 1H), 3.34-3.32 (m, 2H), 2.90 (s, 3H), 2.17 (m, 1H), 2.13-1.94 (m, 2H), 1.73-1.71 (m, 2H), 1.52 (m, 1H), 1.39-1.33 (m, 3H).

Preparation of 1-[1-[2-(2-methoxyphenyl)-2-tetrahydropyran-4-yloxy-ethyl]-5-methyl-6-oxazol-2-yl-2,4-dioxo-thieno[2,3-d]pyrimidin-3-yl]cyclopropanecarboxylic Acid (16331-02)

To a solution of compound 22 (200.00 mg, 343.86 μmol) in H2O (2.00 mL), THF (2.00 mL) and MeOH (2.00 mL), LiOH (41.18 mg, 1.72 mmol) was added. The mixture was heated to 70° C. for 3 hrs. The mixture reaction was acidified to PH 2 with 1M HCl and extracted with EA, the organic phase was dried and concentrated. The residue was purified by column chromatography (DCM/MeOH=20/1) to afford compound 16331-02 (120.00 mg, 211.41 μmol, 61.48% yield) as a yellow solid. $^1$H NMR (400 MHz, CDCl$_3$): δ 7.71 (s, 1H), 7.56-7.54 (m, 1H), 7.32-7.26 (m, 1H), 7.22 (s, 1H), 7.03-7.01 (m, 1H), 6.89-6.84 (m, 1H), 5.43-5.42 (m, 1H), 4.20 (s, 1H), 3.90-3.86 (m, 3H), 3.68-3.65 (m, 2H), 3.40-3.38 (m, 1H), 3.31-3.27 (m, 2H), 2.88 (s, 3H), 2.05-1.96 (m, 2H), 1.69-1.65 (m, 2H), 1.45-1.31 (m, 5H).

Example 4. 1-(6-bromo-1-(2-(2-methoxyphenyl)-2-(tetrahydro-2H-pyran-4-yloxy)ethyl)-5-methyl-2,4-dioxo-1,2-dihydrothieno[2,3-d]pyrimidin-3(4H)-yl) cyclopropanecarboxylic Acid (16331-02)

To a solution of compound 20 (40.00 mg, 67 umol) in H$_2$O (1.00 mL), THF (1.00 mL) and MeOH (1.00 mL), LiOH (11 mg, 0.27 mmol) was added. The mixture was heated to 70° C. for 3 hr.

The mixture reaction was acidified to pH 2 with 1 M HCl and extracted with EA, the organic phase was dried and concentrated. The residue was purified by column chromatography (DCM/MeOH=20/1) to afford compound 16331-02 (15.00 mg) as a yellow solid. $^1$H NMR (400 MHz, DMSO): δ 2.82 (s, 1H), 7.45-7.43 (m, 1H), 7.32-7.30 (m, 1H), 7.03-6.98 (m, 2H), 5.26-5.24 (m, 1H), 3.81 (s, 2H), 3.73 (s, 1H), 3.5 (m, 1H), 3.34 (m, 1H), 3.31-3.25 (m, 2H), 2.35 (s, 3H), 1.73-1.58 (m, 4H), 1.28-1.14 (m, 4H).

Example 5. Methyl-2-(1-(5-methyl-2,4-dioxo-1,2-dihydrothieno[2,3-d]pyrimidin-3(4H)-yl)cyclopropyl)acetate This title compound was prepared according to the following reaction scheme:

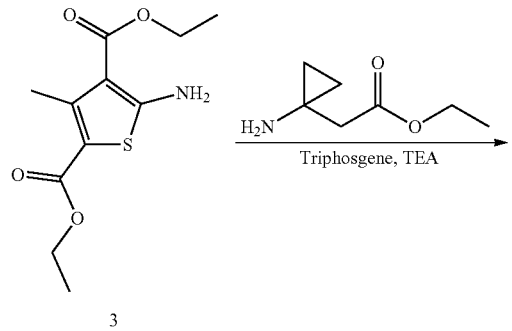

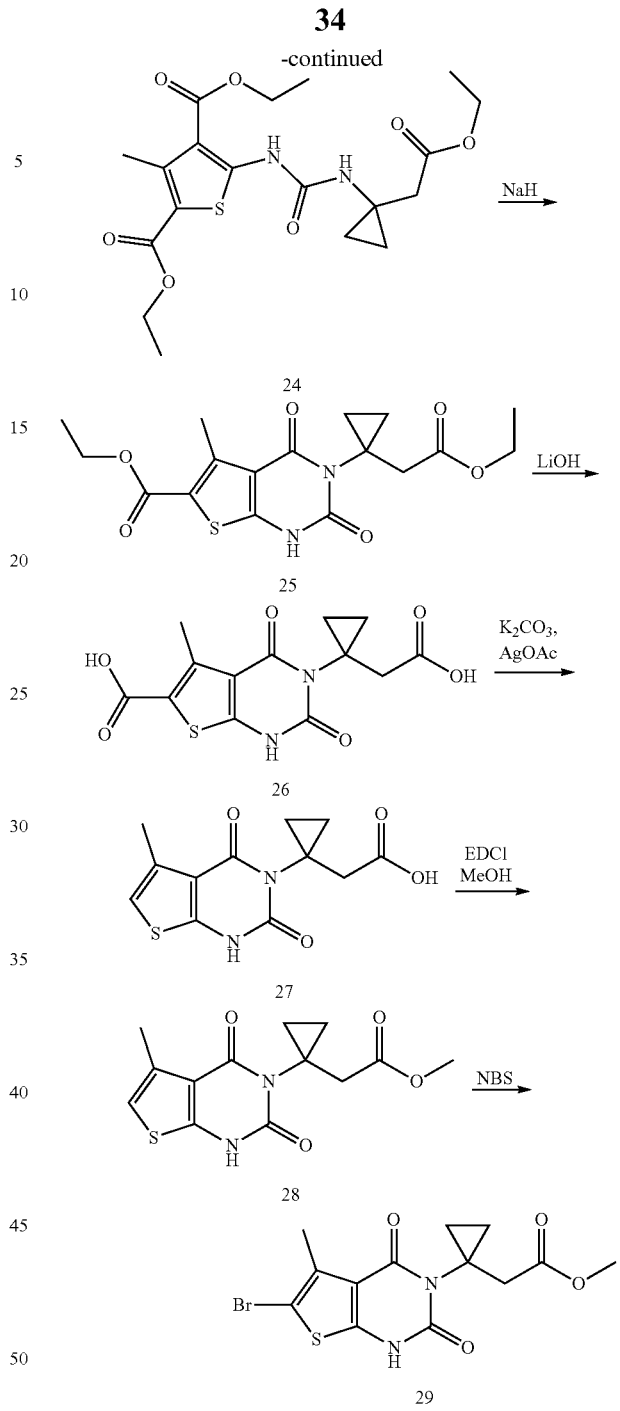

Preparation of diethyl-5-(3-(1-(2-ethoxy-2-oxoethyl)cyclopropyl)ureido)-3-methylthiophene-2,4-dicarboxylate (24)

Triphosgene (5.5 g, 18.66 mmol) was added a solution of compound 3 (8 g, 31.1 mmol) in DCM (50 mL) at 0° C. under N$_2$. The mixture was added dropwise TEA (12.5 g, 124.4 mmol) and was stirred at 0° C. for 2 hrs, ethyl 1-aminocyclopropanecarboxylate (4 g, 31.1 mmol) was added. The mixture was stirred at 0° C. overnight. The mixture reaction was added water and extracted with DCM, the organic layer was washed with brine, dried with Na2SO4 and concentrated. The crude was purified by column chromatography (P/E=8/1) to afford 24 (8 g, 62% yield).

Preparation of ethyl-3-(1-(2-ethoxy-2-oxoethyl)cyclopropyl)-5-methyl-2,4-dioxo-1,2,3,4-tetrahydrothieno[2,3-d]pyrimidine-6-carboxylate (25)

To a solution of compound 24 (2.4 g, 5.6 mmol) in 1,4-dioxane (24.00 mL), NaH (440 mg, 11.2 mmol) was added. The mixture was heated to reflux for 1 hr. The mixture reaction was quenched by saturated NH4Cl aqueous and extracted with EA, the organic layer was concentrated. The crude was purified by column chromatography (P/E=3/1) to afford 25 (1.5 g, 68% yield) as a white solid.

Preparation of 3-(1-(carboxymethyl)cyclopropyl)-5-methyl-2,4-dioxo-1,2,3,4-tetrahydrothieno[2,3-d]pyrimidine-6-carboxylic Acid (26)

To a solution of compound 25 (4.4 g, 11.58 mmol) in H2O/THF (100.00 mL) was added LiOH (2.9 g, 69.5 mmol). The mixture reaction was heated to 80° C. overnight. The mixture reaction was acidified to PH 2 with 1M HCl and extracted with EA, the organic layer was dried and concentrated to afford compound 26 (2.5 g, 67% yield) as a white solid. $^1$H NMR (400 MHz, DMSO): δ 2.70 (s, 3H), 2.51-2.43 (m, 2H), 1.13-0.94 (m, 4H).

Preparation of 2-(1-(5-methyl-2,4-dioxo-1,2-dihydrothieno[2,3-d]pyrimidin-3(4H)-yl)cyclopropyl) acetic Acid (27)

A mixture of compound 26 (2.5 g, 7.71 mmol), K2CO3 (2.4 g, 19.3 mmol) and AgOAc (3.8 g, 23.13 mmol) in NMP (20 mL). The mixture reaction was heated to 110° C. for overnight. The reaction was added water and acidified to PH 2 with 1M HCl. The mixture was extracted with EA, the organic phase dried and concentrated. The residue was purified by column chromatography (DCM/MeOH=10/1) to afford compound 27 (1.5 g, 71% yield) as a yellow solid. $^1$H NMR (400 MHz, DMSO): δ6.65 (s, 1H), 2.50-2.43 (s, 2H), 2.32 (s, 3H), 1.12-1.08 (m, 2H), 0.92 (s, 2H).

Preparation of methyl-2-(1-(5-methyl-2,4-dioxo-1,2-dihydrothieno[2,3-d]pyrimidin-3(4H)-yl)cyclopropyl)acetate (28)

A mixture of compound 27 (100.00 mg, 375.56 μmol) and MeOH (19.16 mg, 1.13 mmol) in DCM (3.00 mL), DMAP (4.59 mg, 37.56 μmol) and EDCl (143.84 mg, 751.12 μmol) was added. The mixture was stirred at rt for 3 hr. The mixture reaction was added water and extracted with DCM, the organic layer was dried and concentrated. The residue was purified by column chromatography (P/E=2/1) to afford compound 28 (70.00 mg, 249.73 μmol, 66.50% yield) as a white solid. $^1$H NMR (400 MHz, DMSO): δ 6.66 (s, 1H), 3.49 (s, 3H), 2.54-2.41 (s, 2H), 2.33 (s, 3H), 1.11-1.08 (m, 2H), 0.93-0.92 (m, 2H).

Preparation of methyl-2-(1-(5-methyl-2,4-dioxo-1,2-dihydrothieno[2,3-d]pyrimidin-3(4H)-yl)cyclopropyl)acetate (29)

To a solution of compound 28 (144 mg, 0.49 mmol) in DMF (10.00 mL) at −10° C., NBS (87 mg, 0.49 mmol) was added. The reaction mixture was stirred at −10° C. for 2 hr. The reaction mixture was added saturated NH4Cl aqueous and extracted with EA, the organic layer was washed with brine, dried and concentrated, The crude was purified by column chromatography (P/E=2/1) to afford compound 29 (0.11 mg, 61% yield) as a white solid. $^1$H NMR (400 MHz, DMSO): δ 3.49 (s, 3H), 2.50 (s, 2H), 2.30 (s, 3H), 1.11-1.08 (m, 2H), 0.93-0.92 (m, 2H).

Example 6. 2-(1-(1-(2-(2-methoxyphenyl)-2-(tetrahydro-2H-pyran-4-yloxy)ethyl)-5-methyl-6-(oxazol-2-yl)-2,4-dioxo-1,2-dihydrothieno[2,3-d]pyrimidin-3(4H)-yl)cyclopropyl)acetic acid (16331-03), and 2-(1-(2-(2-(2-methoxyphenyl)-2-(tetrahydro-2H-pyran-4-yloxy)ethoxy)-5-methyl-6-(oxazol-2-yl)-4-oxothieno[2,3-d]pyrimidin-3(4H)-yl)cyclopropyl) acetic acid (16331-03-ISO)

A mixture of the title isomeric compounds was prepared according to the following reaction scheme:

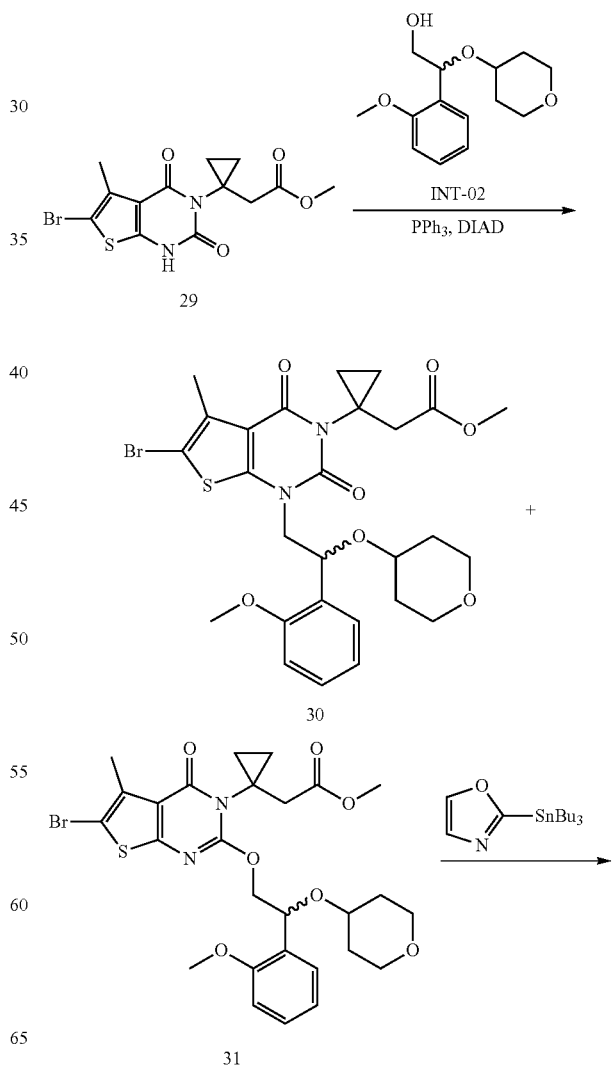

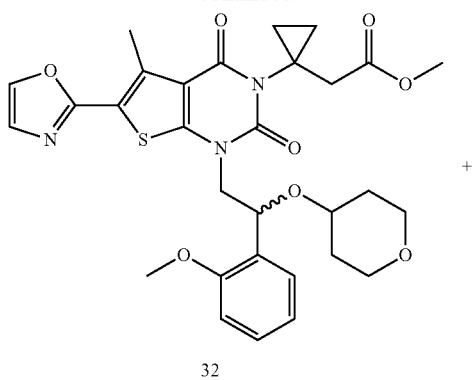

32

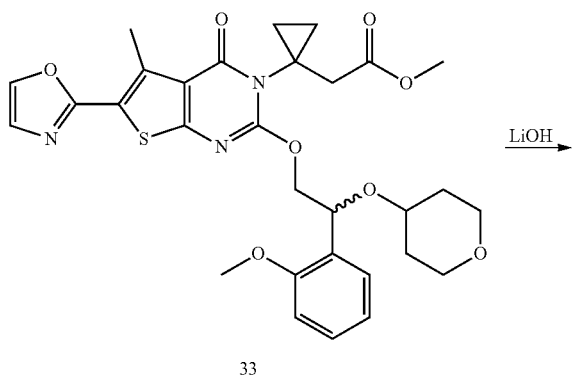

33

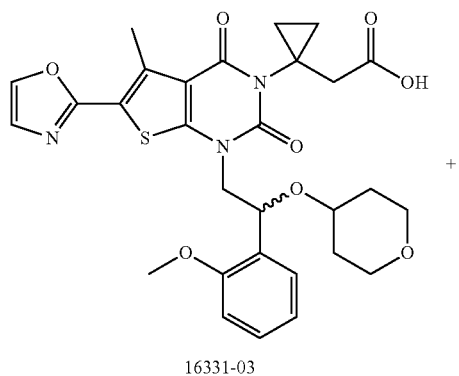

16331-03

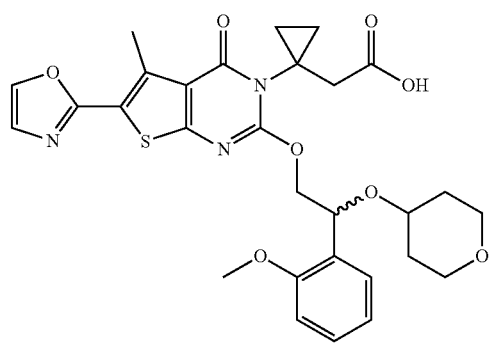

16331-03-ISO

Preparation of methyl-2-(1-(6-bromo-1-(2-(2-methoxyphenyl)-2-(tetrahydro-2H-pyran-4-yloxy)ethyl)-5-methyl-2,4-dioxo-1,2-dihydrothieno[2,3-d]pyrimidin-3(4H)-yl)cyclopropyl)acetate (30) and methyl-2-(1-(6-bromo-2-(2-(2-methoxy phenyl)-2-(tetrahydro-2H-pyran-4-yloxy)ethoxy)-5-methyl-4-oxothieno[2,3-d]pyrimidin-3(4H)-yl)cyclopropyl) acetate (31)

A 100 mL 3-necked round-bottom flask was charged with THF (8.00 mL), compound 9 (330.00 mg, 818.27 μmol), compound 10 (309.69 mg, 1.23 mmol) and PPh₃ (643.87 mg, 2.45 mmol) under N₂, was added DIAD (237.52 mg, 1.80 mmol). The reaction was stirred at rt overnight. The reaction mixture was concentrated and the residue was purified by column chromatography (P/E=15/1) to compound 31 (240.00 mg, 376.42 μmol, 46.0% yield) and 30 (120.00 mg, 188.21 μmol, 23.00% yield) as a white solid.

Preparation of methyl-2-(1-(1-(2-(2-methoxyphenyl)-2-(tetrahydro-2H-pyran-4-yloxy)ethyl)-5-methyl-6-(oxazol-2-yl)-2,4-dioxo-1,2-dihydrothieno[2,3-d]pyrimidin-3(4H)-yl)cyclopropyl)acetate (32) and methyl 2-(1-(2-(2-(2-methoxyphenyl)-2-(tetrahydro-2H-pyran-4-yloxy)ethoxy)-5-methyl-6-(oxazol-2-yl)-4-oxothieno[2,3-d]pyrimidin-3(4H)-yl) cyclopropyl)acetate (33)

To a mixture of compounds 30 and 31 (500 mg, 825 umol) in toluene (25.00 mL) was added Pd(PPh₃)₄(275 mg, 250 umol) under an atmosphere of nitrogen. The mixture was heated to reflux overnight and then concentrated. The residue was purified by preparative HPLC to afford compounds 32 and 33 (together 275 mg, 56% total yield) as a yellow solid.

Preparation of 2-(1-(1-(2-(2-methoxyphenyl)-2-(tetrahydro-2H-pyran-4-yloxy)ethyl)-5-methyl-6-(oxazol-2-yl)-2,4-dioxo-1,2-dihydrothieno[2,3-d]pyrimidin-3(4H)-yl)cyclopropyl)acetic acid (16331-03) and 2-(1-(2-(2-(2-methoxyphenyl)-2-(tetrahydro-2H-pyran-4-yloxy)ethoxy)-5-methyl-6-(oxazol-2-yl)-4-oxothieno[2,3-d]pyrimidin-3(4H)-yl)cyclopropyl) acetic acid (16331-03-ISO)

To a solution of compounds 32 and 33 (275 mg, 462 umol) in H₂O (4.00 mL), THF (4.00 mL) and MeOH (4.00 mL), LiOH (97 mg, 2.12 mmol) was added. The mixture was heated to 70° C. for 3 hr. The mixture reaction was acidified to PH 2 with 1M HCl and extracted with EA, the organic phase was dried and concentrated. The residue was purified by preparative HPLC to afford 16331-03 (23 mg, 9.2% yield) and 16331-03-ISO (30 mg, 11.2% yield) as a yellow solid. 16331-03: $^1$H NMR (400 MHz, CDCl3): δ 7.69 (s, 1H), 7.54 (m, 1H), 7.32 (m, 1H), 7.26 (s, 1H), 7.04-7.02 (m, 1H), 6.92-6.90 (m, 1H), 5.30 (s, 1H), 4.59-4.47 (m, 2H), 3.89-3.87 (m, 2H), 3.86 (m, 3H), 3.38-3.35 (m, 2H), 2.88 (s, 3H), 2.82-2.79 (m, 1H), 2.10-1.95 (m, 1H), 1.85-1.80 (m, 1H), 1.66-1.62 (m, 2H), 1.29-1.18 (m, 4H).

Example 7. 3-(6-bromo-1-((R)-2-(2-methoxyphenyl)-2-((tetrahydro-2H-pyran-4-yl)oxy)ethyl)-5-methyl-2,4-dioxo-1,4-dihydrothieno[2,3-d]pyrimidin-3(2H)-yl)tetrahydro-2H-pyran-3-carboxylic acid (34155)

The title compound was synthesized based on the following scheme:

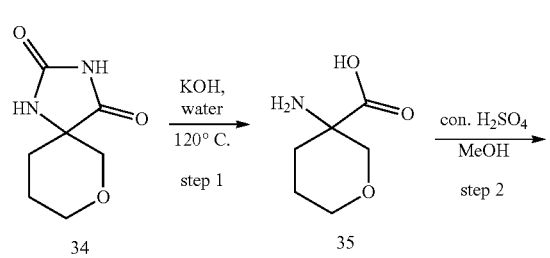

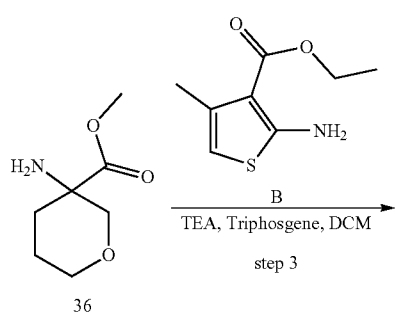

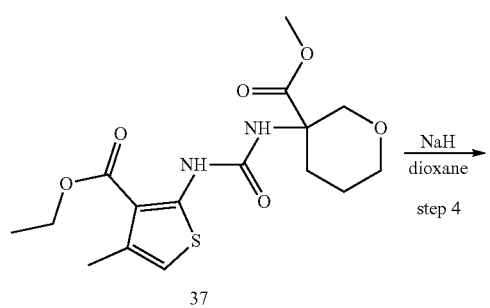

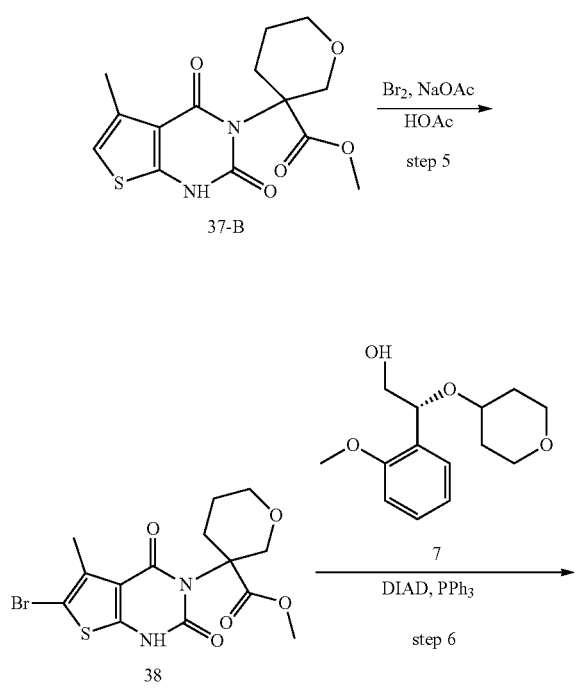

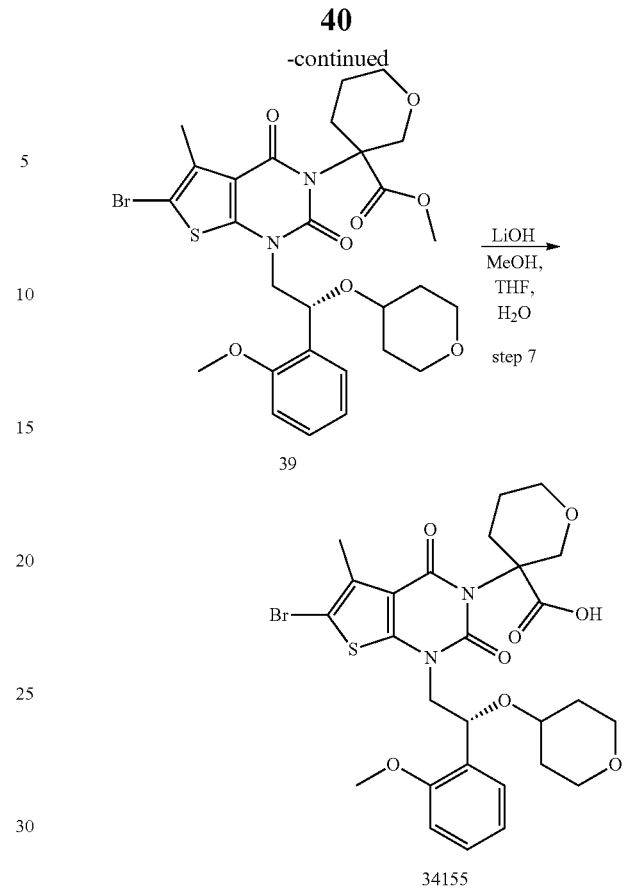

Synthesis of Compound 35

A solution of Compound 34 (30 g, 176 mmol) in 6N KOH (100 mL) was stirred for 14 hours at the reflux temperature, at which time LCMS indicated the reaction was complete. The solution was adjusted to pH 9 with 4.0 N HCl. After removing the solvent under vacuum, Compound 35 was obtained as a white solid (40 g, crude, contains a lot of salt) and used directly for the next step without further purification.

Synthesis of Compound 36

To a solution of Compound 35 (40 g, crude, contains a lot of salt) in methanol (400 mL) was added concentrated H2SO4 (20 mL). This mixture was stirred for 12 hours at reflux temperature, at which time LCMS indicated the reaction was complete. After removing the solvent under vacuum, Compound 36 was obtained as white solid (47 g, crude, purity: 35%), used directly for the next step without further purification.

Synthesis of Compound 37

Into a 100 mL 3-necked round-bottom flask, purged and maintained under an inert atmosphere of nitrogen, was placed Compound B (2.87 g, 18.3 mmol) and DCM (30 mL). This was followed by the addition of ditrichloromethyl carbonate (1.84 g, 7.32 mmol) at 0° C. This was followed by the addition of TEA (6.28 g, 73.2 mmol) dropwise with stirring at 0° C. over 15 min. The resulting solution was stirred for 2 h at 0° C. To this solution was added Compound 36 (8 g, purity:35%), the resulting solution was stirred overnight at room temperature. The reaction was then quenched by the addition of 50 mL of water and extracted with 2×50 mL of DCM. The organic layers were concentrated under vacuum. The crude product was purified by silica gel chromatography (PE/EtOAc=3/1 as eluent) to afford 1.4 g (25%) of Compound 937 as a yellow solid.

$^1$H NMR (400 MHz, CDCl3) δ 10.74 (s, 1H), 6.28 (s, 1H), 5.63 (s, 1H), 4.38-4.33 (m, 2H), 4.00-3.95 (m, 2H), 3.77 (s, 3H), 3.65 (d, J=11.6 Hz, 1H), 3.51-3.45 (m, 1H), 2.47-2.43 (m, 1H), 2.35 (s, 3H), 2.18-2.10 (m, 1H), 1.86-1.70 (m, 1H), 1.62-1.59 (m, 1H), 1.43-1.39 (m, 3H). MS (M+H)+: m/z=371.2.

Synthesis of Compound 37-B

Into a 50 mL three-necked round-bottom flask, purged and maintained under an inert atmosphere of nitrogen, was placed Compound 37 (1.4 g, 3.78 mmol) and dioxane (15 mL). This was followed by the addition of sodium hydride (378 mg, 9.45 mmol, 60% in oil) at 10° C. The resulting solution was stirred for 2 h at 110° C. The reaction solution was cooled to room temperature, and then quenched by the addition of 100 mL NH4Cl (sat., aq.). The resulting solution was extracted with 100 mL x 3 ethyl acetate and the organic layers combined and concentrated under vacuum to afford 16 g crude product. The crude product was purified by silica gel chromatography (PE/EtOAc=3/2 as eluent) to afford 820 mg (67%) of Compound 9-B as a yellow solid.

$^1$H NMR (400 MHz, CDCl3) δ 7.25 (s, 1H), 6.95 (s, 1H), 4.03-3.91 (m, 2H), 3.77 (s, 3H), 3.54-3.53 (m, 1H), 2.39 (s, 3H), 2.27-2.23 (m, 1H), 2.20-2.17 (m, 1H), 1.63-1.59 (m, 1H), 1.24 (s, 2H). MS (M+H)+: m/z=325.1.

Synthesis of Compound 38

Into a 250-mL 3-necked round-bottom flask, was placed Compound 37-B (820 mg, 2.53 mmol), CH3COONa (456 mg, 5.06 mmol) and acetic acid (8 mL). This was followed by the addition of Br$_2$ (364 mg, 2.23 mmol) by dropwise with stirring. The resulting solution was stirred for 0.5 h at room temperature, concentrated under vacuum. The mixture was dissolved with EA (50 mL) and wash with 20 mL Na$_2$CO3(sat. aq.). The EA phase was washed with brine, dried over Na2SO4 and concentrated to afforded 1.3 g crude product. The product was purified with silica gel chromatography (PE/EtOAc=3/2 as eluent) to give 810 mg (79%) of Compound 10 as a yellow solid.

$^1$H NMR (400 MHz, CDCl$_3$) δ 6.52 (s, 1H), 4.05-3.90 (m, 2H), 3.76 (s, 3H), 3.59-3.50 (m, 1H), 2.79 (s, 3H), 2.28-2.21 (m, 1H), 2.20-1.97 (m, 1H), 1.80-1.75 (m, 2H), 1.63-1.59 (m, 1H), 1.24 (s, 2H). MS (M+H)+: m/z=401.1.

Synthesis of Compound 39

Compound 38 reacts with Compound 7 in the presence of DIAD and PPh$_3$ to result in Compound 39.

Synthesis of Title Compound 34155

Compound 39 reacts with LiOH in the mixed solvent of methanol, THF and water to give rise to the title compound 34155.

Additional Exemplary Compounds

The following additional compounds of this invention were prepared in methods similar to those described above, with conversion between acids and amides in methods well known in the art.

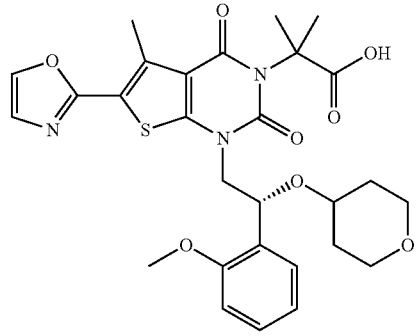

Example 8

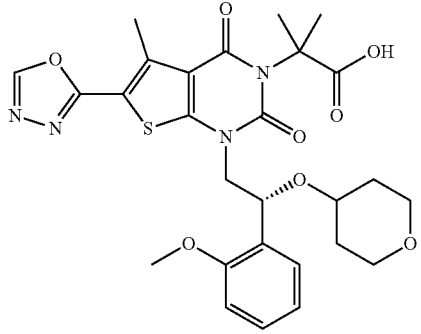

Example 9

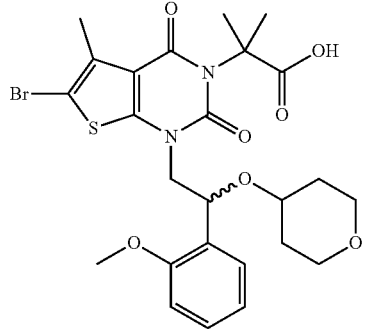

Example 10

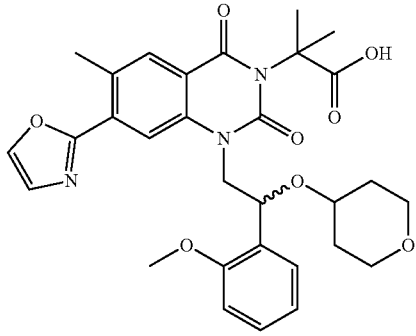

Example 11

Example 12
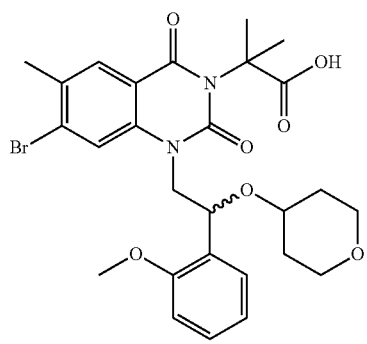
Example 13
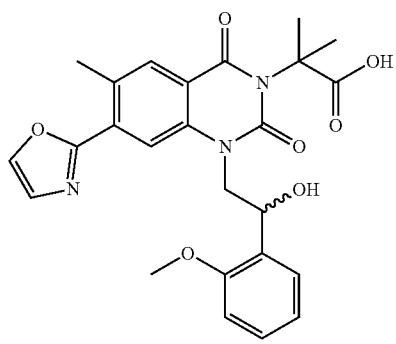
Example 14
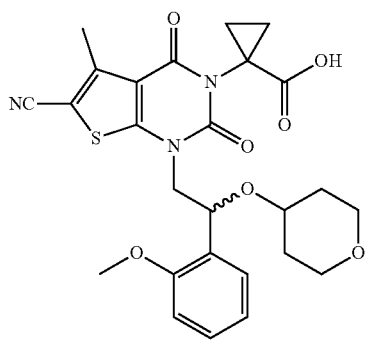
Example 15
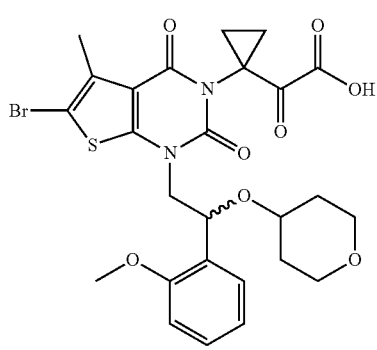
Example 16
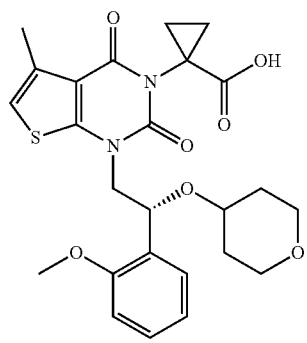
Example 17
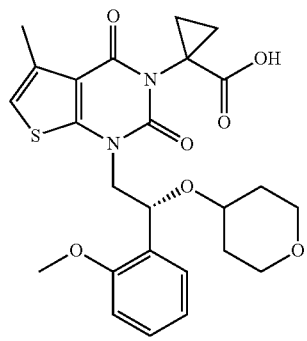
Example 18
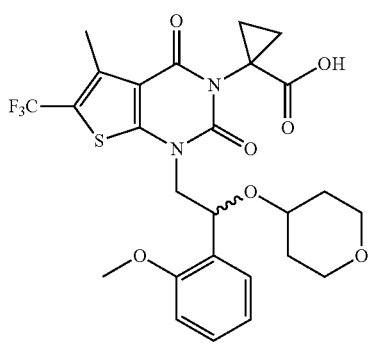
Example 82
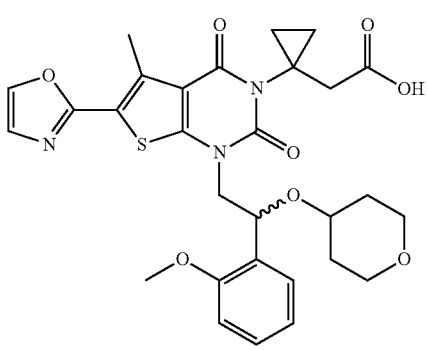

Example 19
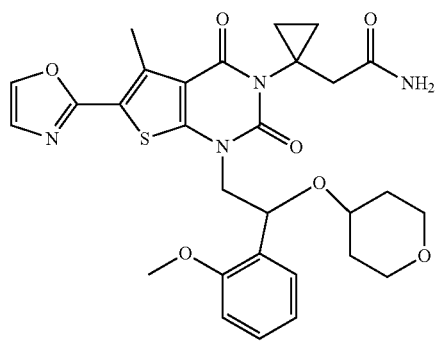
Example 20
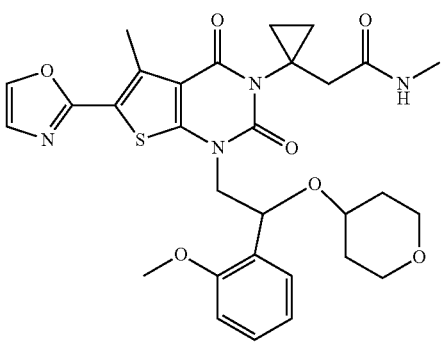
Example 21
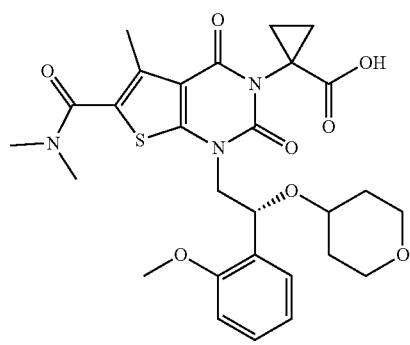
Example 22
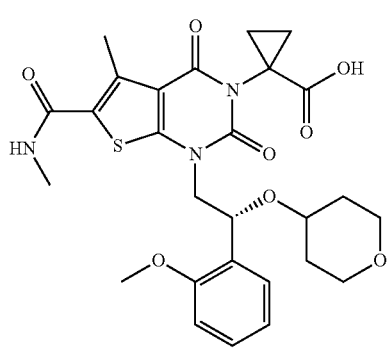
Example 23
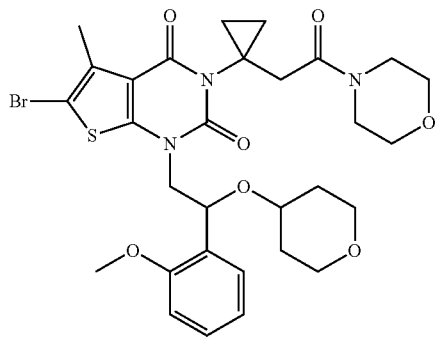
Example 24
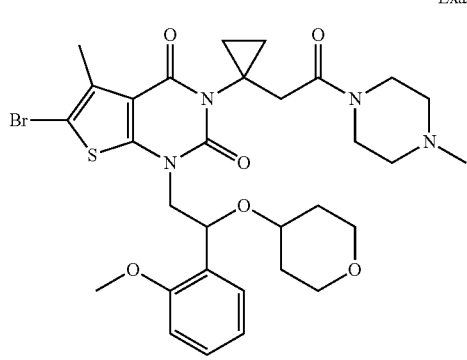
Example 25
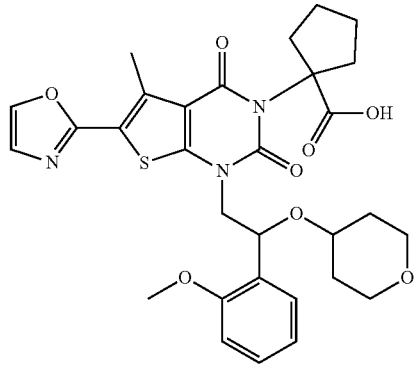
Example 26
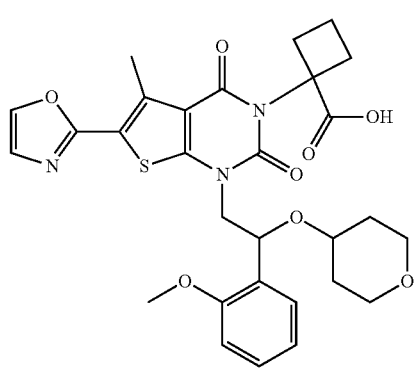

-continued
Example 27
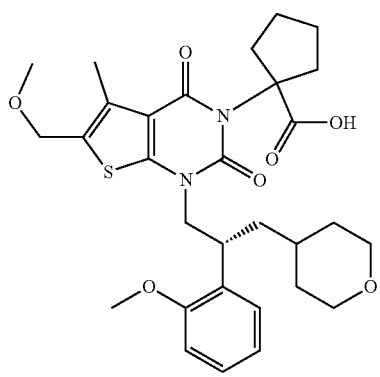
Example 28
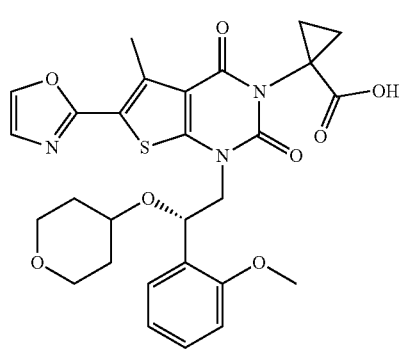
Example 29
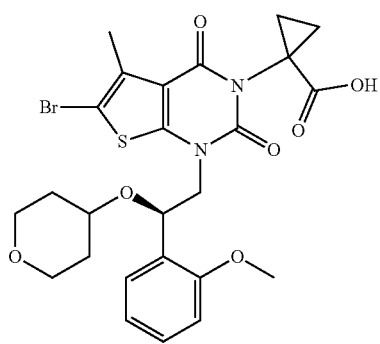
Example 30
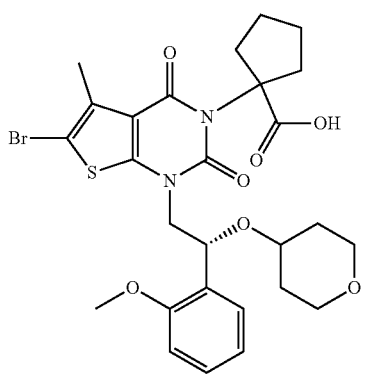
-continued
Example 31
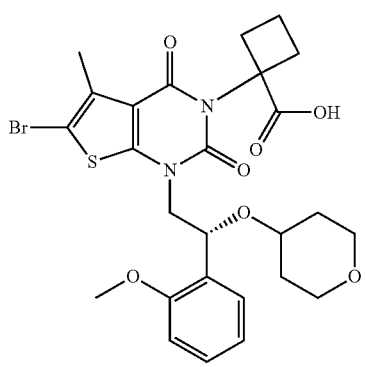
Example 32
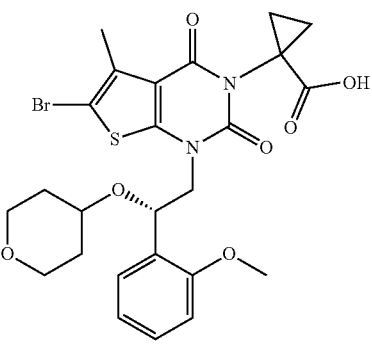
Example 33
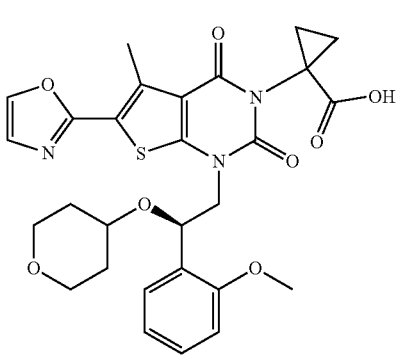
Example 34
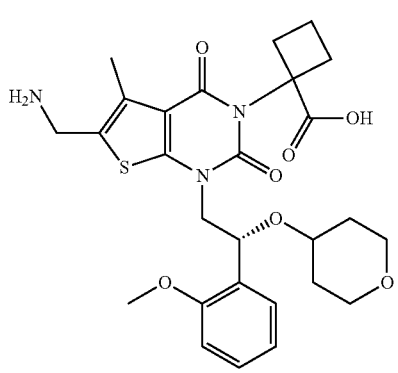

Example 35
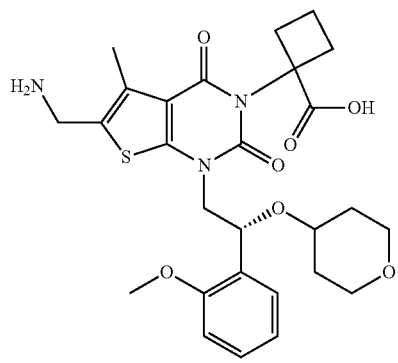
Example 39
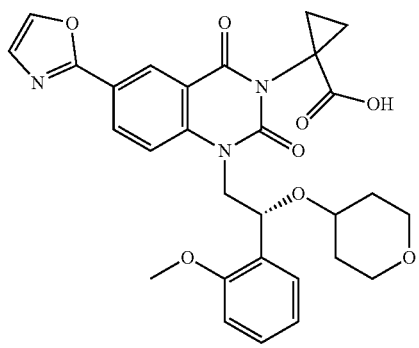
Example 36
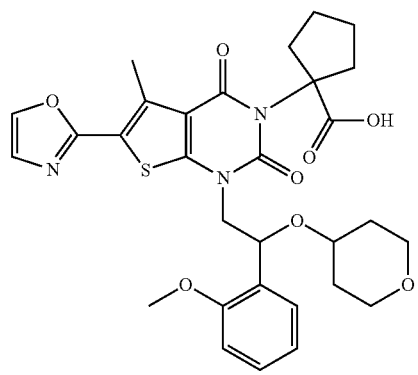
Example 40
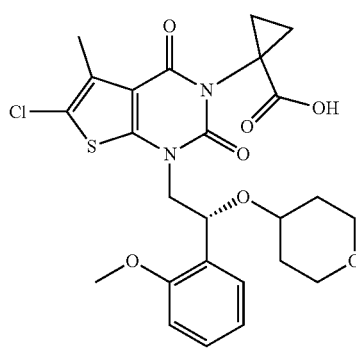
Example 37
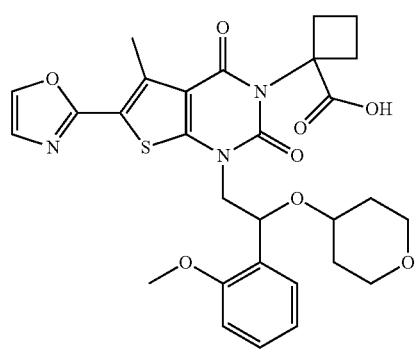
Example 41
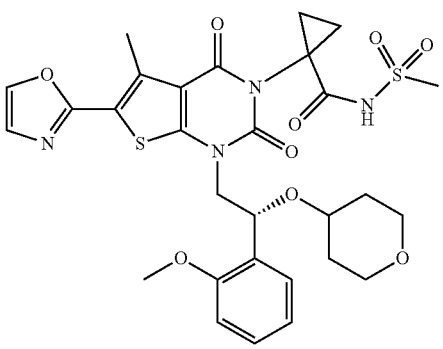
Example 38
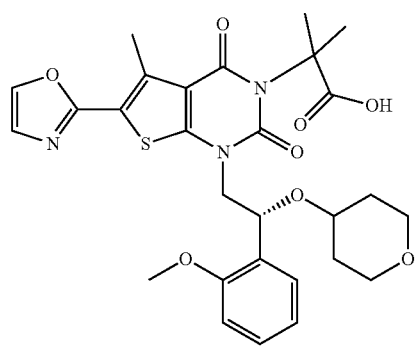
Example 42
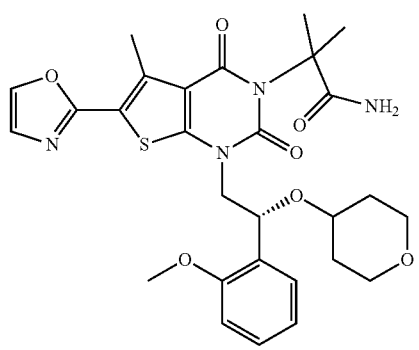

Example 43
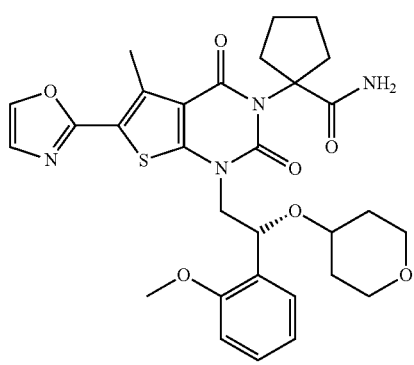
Example 44
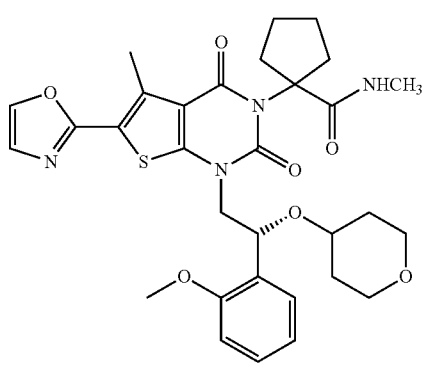
Example 45
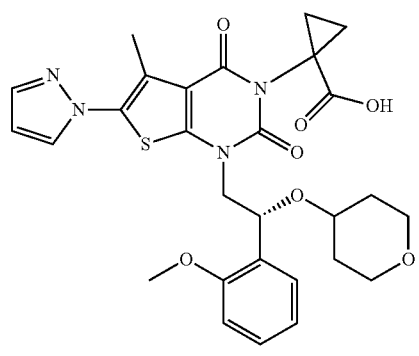
Example 46
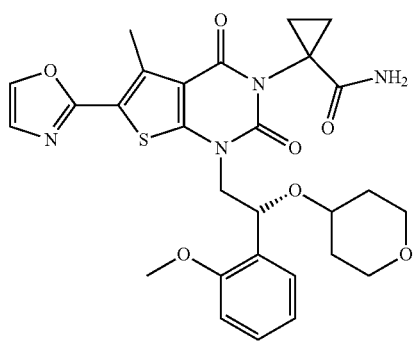
Example 47
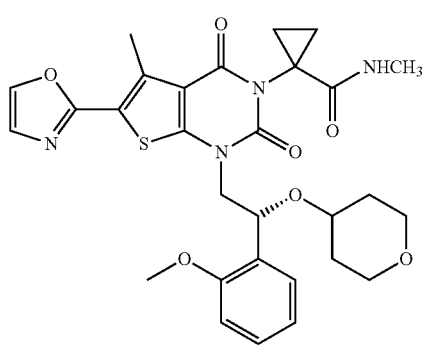
Example 48
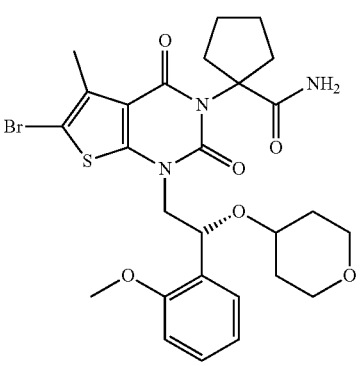
Example 49
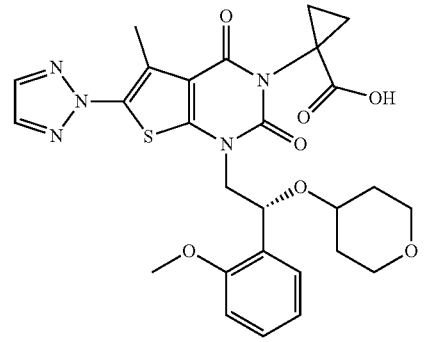
Example 50
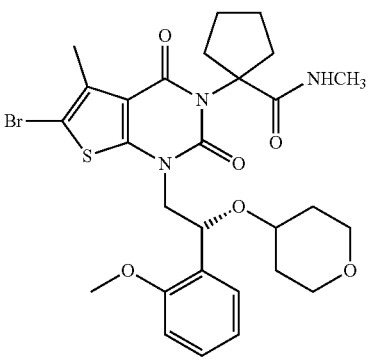

Example 51
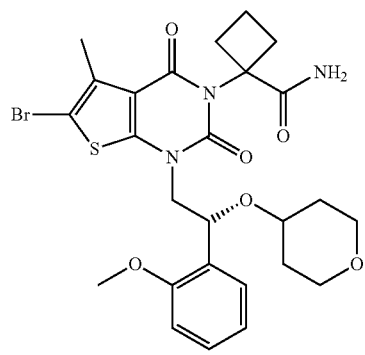
Example 55
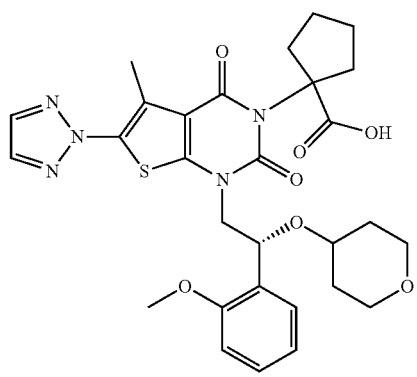
Example 52
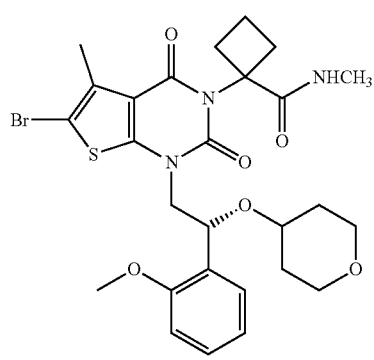
Example 56
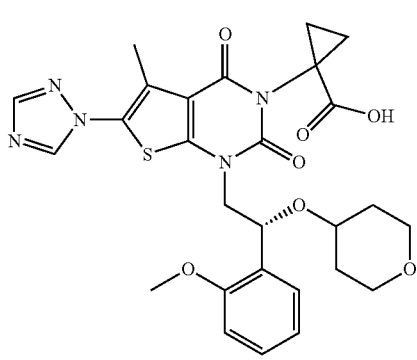
Example 53
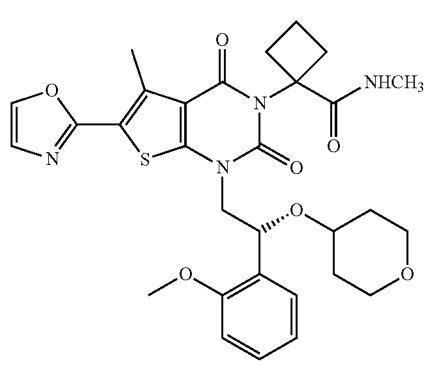
Example 57
Example 54
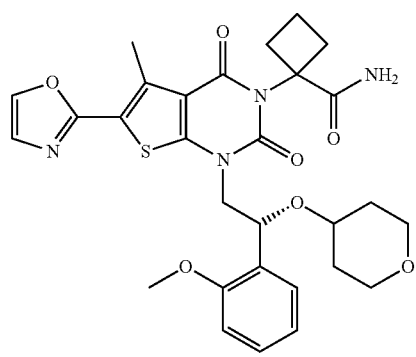
Example 58

Example 59
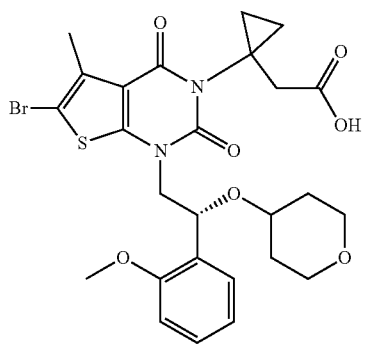
Example 63
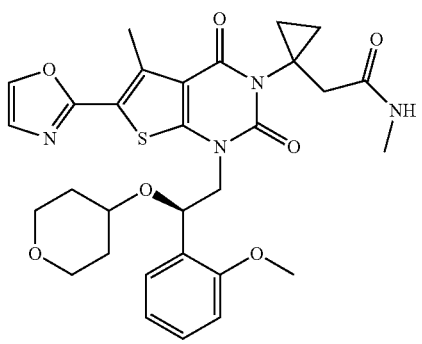
Example 60
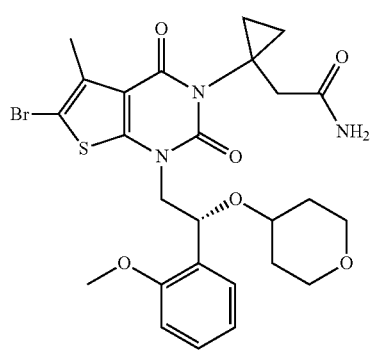
Example 64
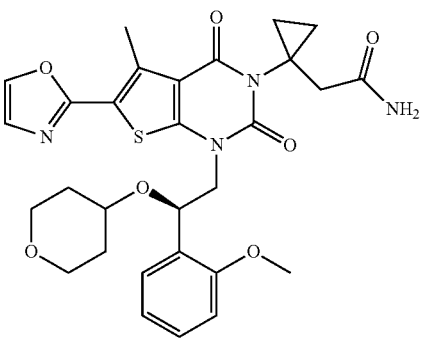
Example 61
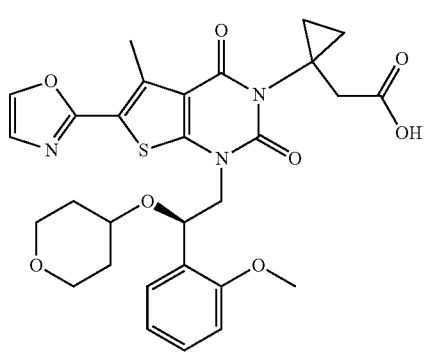
Example 65
Example 62
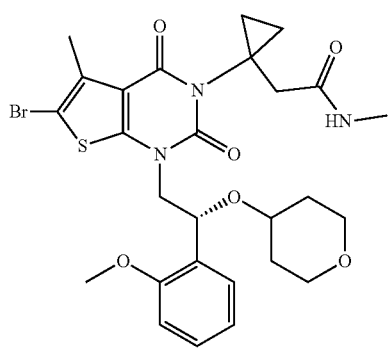
Example 66
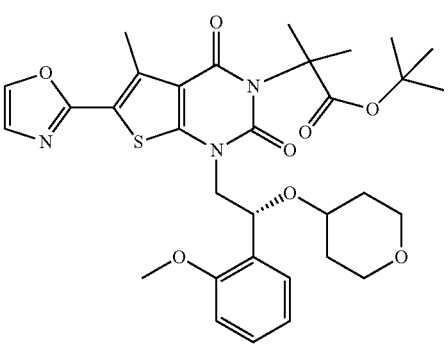

Example 67
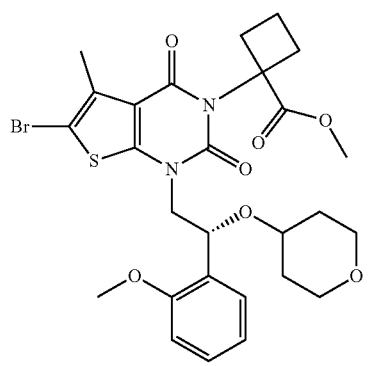
Example 68
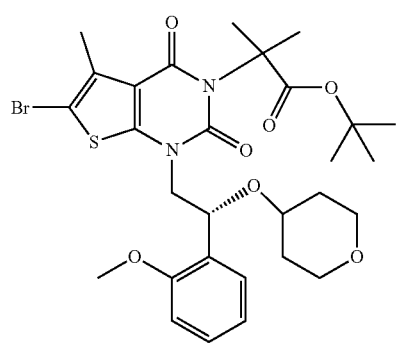
Example 69
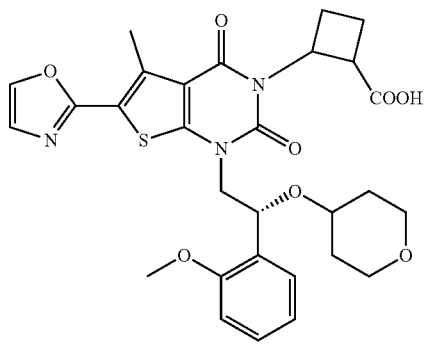
Example 70
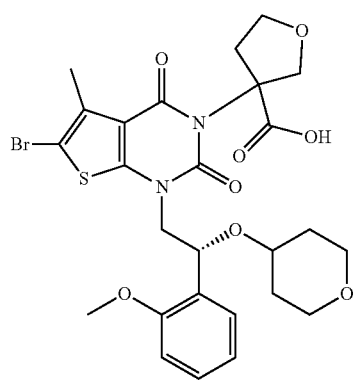
Example 71
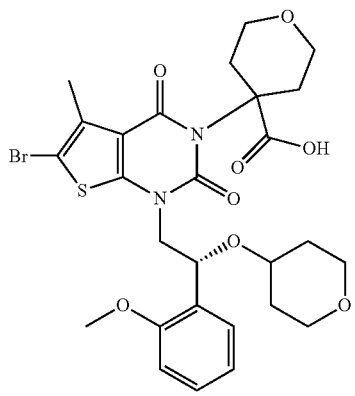
Example 72
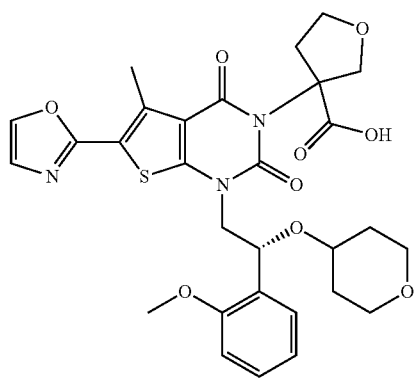
Example 73
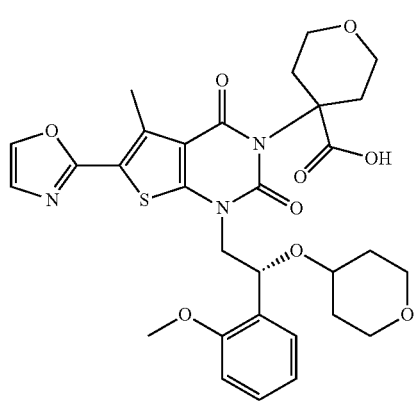
Example 74
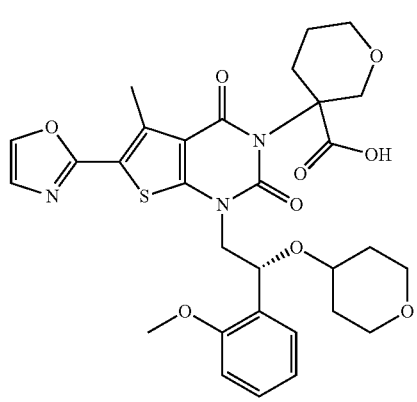

Example 75

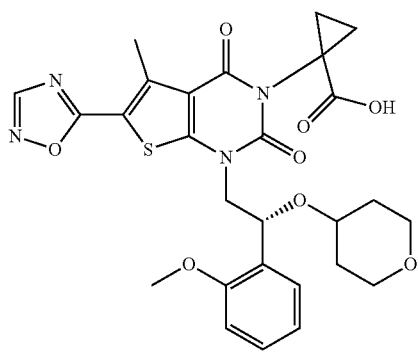

Example 76

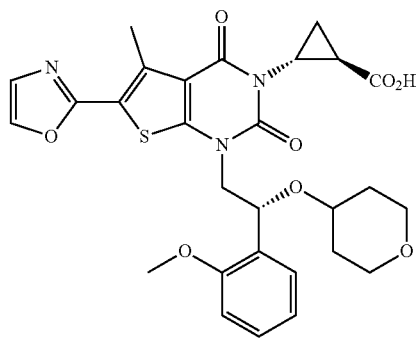

Example 77

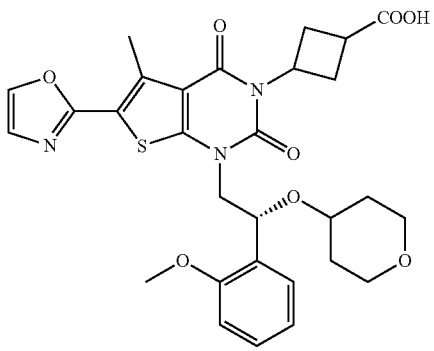

Example 78

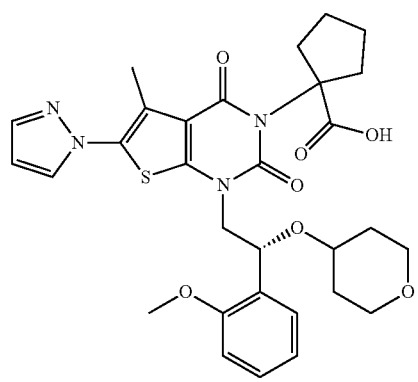

Example 79

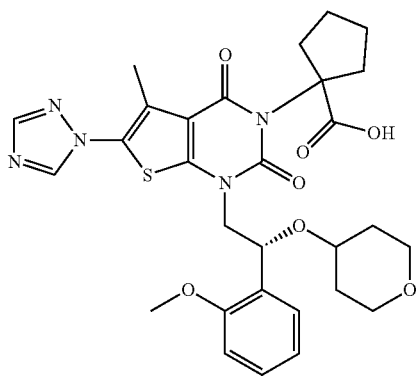

Example 80

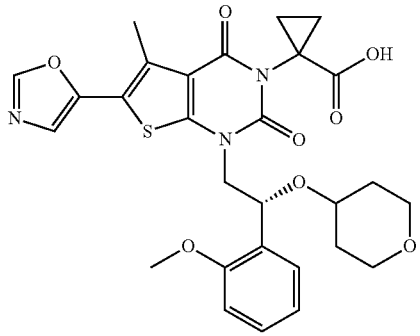

Example 81

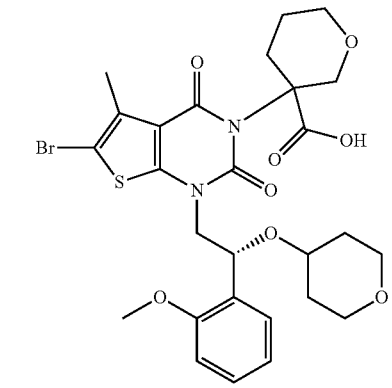

Listed below are some of the physical chemical data of these exemplary compounds (NMR taken at 400 MHz with compound in $CDCl_3$ or DMSO):

Example 25: (MS: 599.66; $^1$H-NMR: 2.862, 3.876, 7.298)
Example 26 (MS: 581.64; $^1$H-NMR: 2.877, 3.909, 7.301, 7.741)
Example 27 (MS: 570.7; $^1$H-NMR: 2.329, 3.390, 3.729, 4.527, 7.278)
Example 28 (MS: 567.61; $^1$H-NMR: 1.428, 2.868, 3.330, 3.853, 3.919, 4.867, 7.303, 8.005)
Example 29 (MS: 579.46; $^1$H-NMR: 2.434, 3.330, 3.823, 3.892, 4.869)
Example 30 (MS: 607.51; $^1$H-NMR: 2.211, 2,417, 3.850, 7.270)
Example 31 (MS: 593.09; $^1$H-NMR: 2.242, 3.203, 3.733, 4.764)
Example 32 (MS: 579.46; $^1$H-NMR: 2.302, 3.197, 3.693, 3.757, 4.757)
Example 33 (MS: 567.61; $^1$H-NMR: 2.865, 3.321, 3.852, 3.917, 4.883, 7.301, 8.004)
Example 34 (MS: 543.63; $^1$H-NMR: 1,533, 2.593, 3.329, 3.880, 4.329, 4.882, 7.015)

Example 35 (MS: 543.63)
Example 36 (MS: 595.66; $^1$H-NMR: 2.844, 3.863, 7.261, 7.720)
Example 37 (MS: 581.18; $^1$H-NMR: 2.832, 3.325, 3.894, 4.865, 7.300, 8.000)
Example 38 (MS: 569.63; $^1$H-NMR: 1.250, 1.838, 1.873, 2.854, 3.865, 7.266)
Example 39 (MS: 547.56; $^1$H-NMR: 1.265, 1.395, 1.613, 1,899, 3.299, 3.820, 3.927, 4.850, 7.057, 7.356, 8.050, 8.774)
Example 40 (MS: 535.01; $^1$H-NMR: 2.426, 3.323, 4.856)
Example 41 (MS: 644.16; $^1$H-NMR: 2.872, 3.241, 3.326, 4.884)
Example 42 (MS: 568.64; $^1$H-NMR: 1.899, 1.912, 2.861, 3.876, 7.272, 7.740)
Example 43 (MS: 594.68; $^1$H-NMR: 1.827, 2.874, 3.833, 7.305, 7.760)
Example 44 (MS: 608.23; $^1$H-NMR: 1.773, 2.122, 2.867, 3.884, 7.319, 7.745)
Example 45 (MS: 566.63; $^1$H-NMR: 2.391, 3.323, 3.810, 3.883, 4.884, 7.791)
Example 46 (MS: 566.63; $^1$H-NMR: 1.665, 2.741, 3.210, 3.701, 3.790, 4.750, 7.183)
Example 47 (MS: 580.65; $^1$H-NMR: 1.771, 2.580, 2.731, 3.209, 3.694, 3.789, 4.762, 7.192)
Example 48 (MS: 606.52; $^1$H-NMR: 1.195, 1.679, 2.335, 3.765, 7.193)
Example 49 (MS: 567.61; $^1$H-NMR: 2.633, 3.323, 4.971, 7.973)
Example 50 (MS: 620.56; $^1$H-NMR: 1.701, 2.319, 2.736, 2.816, 7.184)
Example 51 (MS: 592.5; $^1$H-NMR: 2.394, 3.322, 3.960, 5.010)
Example 52 (MS: 606.53; $^1$H-NMR: 2.391, 2.715, 3.322, 3.850, 4.980)
Example 53 (MS: 594.68; $^1$H-NMR: 2.731, 2.834, 3.398, 4.802)
Example 54 (MS: 580.65; $^1$H-NMR: 2.830, 3.323, 3.871, 4.953, 7.297, 8.003)
Example 55 (MS: 595.67; $^1$H-NMR: 2.586, 3.787, 7.166, 7.765)
Example 56 (MS: 567.61; $^1$H-NMR: 2.283, 3.720, 4.850, 6.861, 8.122, 8.753)
Example 57 (MS: 592.5; $^1$H-NMR: 1.215, 2,440, 2.674, 3.391, 4.900)
Example 58 (MS: 578.48; $^1$H-NMR: 2.413, 3.324, 3.855, 4.900)
Example 59 (MS: 593.49; $^1$H-NMR: 1.233, 2.299, 3.206, 4.756)
Example 60 (MS: 592.5; $^1$H-NMR: 1.211, 2.299, 2.482, 2.724, 3.209, 3.682, 3.720, 4.750)
Example 61 (MS: 581.64; $^1$H-NMR: 2.825, 3.332, 3.873, 4.850, 5.419, 7.016, 7.294, 7.968)
Example 62 (MS: 606.53; $^1$H-NMR: 2.397, 2,681, 3.343, 3.776, 3.821, 4.850)
Example 63 (MS: 594.68; $^1$H-NMR: 1.285, 2.692, 2.838, 3.302, 3,791, 3.862, 4.850, 7.295, 7.974)
Example 64 (MS: 580.65; $^1$H-NMR: 2.861, 3.359, 4.850)
Example 65 (MS: 638.73; $^1$H-NMR: 2.848, 3.306, 3.797, 3.860, 4.850, 7.210, 7.971)
Example 66 ($^1$H-NMR: 0.977, 1.484, 1.752, 1.772, 2.829, 3.321, 3.874, 4.850, 7.294, 7.994)
Example 67 (MS: 625.73; $^1$H-NMR: 2.272, 3.201, 3.674, 3.746, 4.752)
Example 68 (MS: 581.64; $^1$H-NMR: 1.439, 1.752, 2.392, 3.329, 3.840, 4.853)
Example 69 (MS: 581.64; $^1$H-NMR: 2.882, 3.360, 3.844, 4.850, 7.286, 7.989)
Example 70 (MS: 608.08)
Example 71 (MS: 622.1)
Example 72 (MS: 597.64)
Example 73 (MS: 611.66)
Example 74 (MS: 611.66)
Example 75 (MS: 568.60)
Example 76 (MS: 567.61)
Example 77 (MS: 581.64)
Example 78 (MS: 594.21)
Example 79 (MS: 595.21)
Example 80 (MS: 567.12)
Example 81 (MS: 623.51)

Compounds of this invention are assayed as inhibitors of ACC using methods known in the art including those contained in Harwood et al. Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals, J. Biol. Chem., 2003, vol. 278, 37099-37111. In some embodiments the assays used are selected from an in vitro ACC enzyme inhibition assays, in vitro cell culture assays, and in vivo efficacy assays in animals. In some embodiments, assay results for compounds of the present invention are compared to results obtained for known inhibitors of ACC or related enzymes.

Compounds of the present invention were evaluated in an in vitro ACC inhibition assay as described by Harwood, et al, 2003, the entirety of which is incorporated herein by reference.

In Vitro Acetyl-CoA Carboxylase (ACC) Inhibition Assay

An exemplary procedure for the in vitro ACC inhibition assay, which can be used to determine the inhibitory action of compounds of the invention toward either ACC1 or ACC2, follows. The ADP-Glo™ Kinase Assay kit from Promega was used. The ADP-Glo™ Kinase Assay is a luminescent ADP detection assay to measure enzymatic activity by quantifying the amount of ADP produced during an enzyme reaction. The assay is performed in two steps; first, after the enzyme reaction, an equal volume of ADP-Glo™ Reagent is added to terminate the reaction and deplete the remaining ATP. Second, the Kinase Detection Reagent is added to simultaneously convert ADP to ATP and allow the newly synthesized ATP to be measured using a luciferase/luciferin reaction. Luminescence can be correlated to ADP concentrations by using an ATP-to-ADP conversion curve. The detailed procedure is as follows. 50 µL of the compound being tested (600 uM in DMSO) was added to a 384-well dilution plate. The compound was diluted 1:3 in succession in DMSO for each row for 11 wells. 0.5 µL ACC2 working solution was added to 384-well white Optiplate assay plate. 0.5 µL diluted compound solution in each column from step 2 to assay plate, each row containing 2 replicates. For the last 2 rows, add 0.5 µL negative control (DMSO) in one row and 0.5 µL positive control (compound 1-97) in the other. The plates were incubated at room temperature for 15 minutes. 5 µL substrate working solution was added to each well to initiate reaction. Final ACC2 reaction concentrations consist of: 5 nM ACC2, 20 µM ATP, 20 µM acetyl-CoA, 12 mM NaHCO$_3$, 0.01% Brij35, 2 mM DTT, 5% DMSO, test compound concentrations: 30 µM, 10 µM, 3.33 µM, 1.11 µM, 0.37 µM, 0.123 µM, 0.0411 µM, 0.0137 µM, 0.00457 µM, 0.00152 µM, and 0.00051 µM. Plates were incubated at room temperature for 60 minutes. 10 µL ADP glo reagent was added. Plates were incubated at room temperature for 40 minutes. 20 μL kinase detection reagent was added. Plates were incubated at room temperature for 40 minutes, then read on a Perkin Elmer EnVision 2104 plate reader for luminescence as Relative Light Units (RLU).

Data for each concentration, as well as the positive and negative controls were averaged, and the standard deviation calculated. Percent inhibition was calculated by the formula: 100×(average negative control-compound)/(average negative control-average positive control). The IC50 for each compound was calculated by fitting the data with a non-linear regress ion equation: Y=Bottom+(Top−Bottom)/(1+ 10((Log IC50−X* HillSlope)), where X is the log of compound concentration and Y is percent inhibition.

As shown in the following table, tested compounds of this invention generally exhibited inhibitory effect on ACC and possesses other significant biological activities:

| Example No. | $IC_{50}$ (μM) ACC1 (A: <0.001; B: 0.001-0.01; C: 0.01-0.05; D: >0.05) | $IC_{50}$ (μM) ACC2 (A: <0.01; B: 0.01-0.1; C: 0.1-1.0; D: >1.0) | $IC_{50}$ (μM) ND630/RJ-cmps(%) (A: <0.003 B: 0.003-0.005; C: 0.005-0.01; D: >0.01) | $EC_{50}$ (μM) HepG2 (A: <0.01; B: 0.01-0.1; C: 0.1-1.0; D: >1.0) | $EC_{50}$ (μM) ND630/RJ-cmps(%) (A: <0.01; B: 0.01-0.1; C: 0.1-1.0; D: >1.0) | $EC_{50}$ (μM) MDA-MB-468 (cisplatin: 0.68 μm) (A: <1.0; B: 1.0-10; C: >10) | $EC_{50}$ (μM) A549 (cisplatin: 1.28 μm) (A: <0.5; B: 0.5-1.0; C: >1.0) |
|---|---|---|---|---|---|---|---|
| 8 |  | B | C | D | D |  |  |
| 3 |  | B | C | B | D |  |  |
| 4 |  | B | C | B | D |  |  |
| 9 |  | C | C | D | D |  |  |
| 10 |  | B | C | C | D |  |  |
| 82 |  | B | C | B | D |  |  |
| 11 |  | D | C | / | B |  |  |
| 12 |  | D | C | / | B |  |  |
| 13 |  | D | C | / | B |  |  |
| 14 |  | C | C | D | B |  |  |
| 15 |  | C | C | C | B |  |  |
| 16 |  | D | C | / |  |  |  |
| 17 |  | D | C | / |  |  |  |
| 18 |  | D | C |  |  |  |  |
| 80 |  | B | C | D | D |  |  |
| 19 |  | B | C | A | D |  |  |
| 20 |  | B | C | B | D |  |  |
| 21 |  | D | C | / | C |  |  |
| 22 |  | C | C | / | C |  |  |
| 23 |  | C | B | / | C |  |  |
| 24 |  | C | B | / | C |  |  |
| 25 |  | A | B | / | C |  |  |
| 26 |  | A | B | / | C |  |  |
| 27 |  | D | B | / | C |  |  |
| 28 |  | C | B | / | C |  |  |
| 29 | B | A | B | B | C | C | B |
| 30 |  | A | B | C | D | C | C |
| 31 | B | A | B | B | D | C | A |
| 32 |  | C | B | / | C |  | / |
| 33 | A | A | B | B | D | B | A |
| 34 |  | D | B | / | C |  | / |
| 35 |  | D | B | / | C | / | / |
| 36 | B | A | B | B | D | C | B |
| 37 | A | A | C | B | D | C | A |
| 38 | A | A | C | B | D | C | A |
| 39 |  | D | C | C | B | / | / |
| 40 |  | B | C | C | D | C | C |
| 41 |  | A | C | D | D | B | A |
| 42 | A | A | C | A | D | C | A |
| 43 | B | A | C | A | D |  |  |
| 44 | B | B | C | A | D |  |  |
| 45 |  | A | C | C | D |  |  |
| 46 | B | B | C | B | D |  |  |
| 47 | B | B | C | B | D |  |  |
| 48 |  | A | B | C | D |  |  |
| 49 |  | A | B | C | C |  |  |
| 50 |  | B | B | C | C |  |  |
| 51 | C | B | B | B | D |  |  |
| 52 | C | B | B | B | D |  |  |
| 53 | B | A | B | B | D |  |  |
| 54 | B | B | C | A | D |  |  |
| 55 | A | A | C | A | D |  |  |
| 56 |  | C | C |  |  |  |  |
| 57 |  | C | C | C |  |  |  |
| 58 | C | B | D | D |  |  |  |
| 59 | C | B | D |  |  |  |  |
| 60 | C | B | D |  |  |  |  |
| 61 | C | A |  | C | D |  |  |
| 62 | B | B |  | B | D |  |  |
| 63 | B | B |  | B | D |  |  |
| 64 | B | A |  | A | D |  |  |
| 65 |  | B |  | D |  |  |  |

-continued

| Example No. | IC$_{50}$ (μM) ACC1 (A: <0.001; B: 0.001-0.01; C: 0.01-0.05; D: >0.05) | IC$_{50}$ (μM) ACC2 (A: <0.01; B: 0.01-0.1; C: 0.1-1.0; D: >1.0) | IC$_{50}$ (μM) ND630/RJ-cmps(%) (A: <0.003 B: 0.003-0.005; C: 0.005-0.01; D: >0.01) | EC$_{50}$ (μM) HepG2 (A: <0.01; B: 0.01-0.1; C: 0.1-1.0; D: >1.0) | EC$_{50}$ (μM) ND630/RJ-cmps(%) (A: <0.01; B: 0.01-0.1; C: 0.1-1.0; D: >1.0) | EC$_{50}$ (μM) MDA-MB-468 (cisplatin: 0.68 μm) (A: <1.0; B: 1.0-10; C: >10) | EC$_{50}$ (μM) A549 (cisplatin: 1.28 μm) (A: <0.5; B: 0.5-1.0; C: >1.0) |
|---|---|---|---|---|---|---|---|
| 66 | B | B | D | | | | |
| 67 | D | C | D | | | | |
| 68 | D | C | D | | | | |
| 69 | A | A | D | A | D | | |

Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit ACC, in a biological sample or in a patient. In certain embodiments, the amount of compound in compositions of this invention is such that is effective to measurably inhibit ACC, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ACC.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first committed step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carnitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in liver and skeletal muscle [Harwood, 2005].

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation [Tong and Harwood, J. Cellular Biochem., 99: 1476, 2006]. This compartmentalization of malonyl-CoA results from a combination of synthesis proximity [Abu-Elheiga et al., PNAS (USA) 102: 12011, 2005] and the rapid action of malonyl-CoA decarboxylase [Cheng et al., J. Med. Chem., 49:1517, 2006].

Simultaneous inhibition of the enzymatic activities of ACC1 and ACC2 offers the ability to inhibit de novo FA production in lipogenic tissues (e.g., liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of direct inhibition of ACC activity as an important therapeutic target for treating obesity, diabetes, insulin resistance, and the metabolic syndrome.

Abu-Elheiga et al. [Proc. Natl. Acad. Sci. USA 100: 10207-10212, 2003] demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al. [J. Clin. Invest. 116: 817, 2006], using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expression were suppressed than when either ACC1 or ACC2 expression alone was suppressed.

Harwood et al. [J. Biol. Chem. 278: 37099, 2003] demonstrated that the isozyme-nonselective ACC inhibitor, CP-640186, which equally inhibits ACC1 and ACC2 (IC50=60 nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. [Diabetes 55:A288, 2006] demonstrated stimulation of insulin sensitivity in insulin-resistant rat muscle tissue by CP-640186 within 30 min of compound administration, and studies by Furler et al. [Diabetes 55:A333, 2006] used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, ACC inhibitors both reduce de novo lipid synthesis and promote the oxidation of existing fat. This dual effect on lipid metabolism raises the possibility that ACC inhibitors will be substantially more effective in reducing excess fat than other mechanisms. Furthermore, ACC inhibitors will impact insulin sensitivity, plasma and tissue triglycerides, and fasting plasma glucose as a consequence of whole-body and tissue-specific fat mass reduction without the need for poly-pharmacy.

ACC inhibitors need only access the liver and muscle in the peripheral compartment. Avoiding the CNS will address many of side effects associated with the late-stage obesity programs targeting CNS receptors. ACC inhibitors are also expected to have superior safety profiles to existing metabolic disease agents. For example, it is unlikely that an ACC inhibitor will precipitate life-threatening hypoglycemia as is often seen with insulin mimetics, insulin secretagogues, and insulin degradation inhibitors. Also, since ACC inhibitors will reduce whole-body fat mass, they will be superior to the glitazones that increase whole-body fat mass as part of their mechanism of action.

A peripherally acting agent that causes significant weight loss and improves other metabolic endpoints fits well within the US FDA's requirements for approval of a new obesity agent. However, if an approval for obesity continues to be challenging in 5-7 years, ACC inhibitors could be approved for familial combined hyperlipidemia and non-alcoholic steatohepatitis (NASH). There are currently no marketed ACC inhibitors, so an isozyme-nonselective ACC inhibitor would represent first-in-class therapy for treating obesity and metabolic syndrome.

The activity of a compound utilized in this invention as an inhibitor of ACC or treatment for obesity or metabolic syndrome, may be assayed in vitro or in vivo. An in vivo assessment of the efficacy of the compounds of the invention may be made using an animal model of obesity or metabolic syndrome, e.g., a rodent or primate model. Cell-based assays may be performed using, e.g., a cell line isolated from a tissue that expresses ACC. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate in vitro assays quantitate the ability of the inhibitor to bind to protein or nucleic acid molecules within the cell. Inhibitor binding may be measured by radiolabelling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an inhibitor of ACC are set forth in the Examples below. The aforementioned assays are exemplary and not intended to limit the scope of the invention. The skilled practitioner can appreciate that modifications can be made to conventional assays to develop equivalent assays that obtain the same result.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The compounds and compositions, according to the method of the present invention, may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, the compounds and compositions, according to the method of the present invention, may be administered using any amount and any route of administration effective for treating or lessening the severity of a disease associated with ACC (Tong et al. "Acetyl-coenzyme A carboxylase: crucial metabolic enzyme and attractive target for drug discovery" Cell and Molecular Life Sciences (2005) 62, 1784-1803).

In some embodiments, the compounds and compositions, according to the method of the present invention, may be administered using any amount and any route of administration effective for treating or lessening the severity of a metabolic disorder, disease, or condition. In some embodiments, the metabolic disorder is obesity, metabolic syndrome, diabetes or diabetes-related disorders including Type 1 diabetes (insulin-dependent diabetes mellitus, IDDM) and Type 2 diabetes (non-insulin-dependent diabetes mellitus, NIDDM), impaired glucose tolerance, insulin resistance, hyperglycemia, diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, hypertension, insulin resistance, diabetes (including Type 1 and Type 2 diabetes), coronary artery disease, and heart failure. In some embodiments, the metabolic disorder, disease or condition is non-alcoholic fatty liver disease or hepatic insulin resistance.

In some embodiments, the present invention provides a method of treating a metabolic disorder, disease, or condition described herein, comprising administering a compound of the invention in conjunction with one or more pharmaceutical agents. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be used in conjunction with compounds of the present invention include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with compounds of the present invention include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with compounds of the present invention include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-HT2C agonists (e.g. lorcaserin/Belviq), melanin concentrating hormone antagonists, leptin, leptin analogs, leptin agonists, galanin antagonists, lipase inhibitors (e.g. tetra hydrolipstatin/Orlistat), anorectic agents (e.g. bombesin agonists), NPY antagonists (e.g. velneperit), PYY3-36 (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buprorion plus zonisamide (Empatic), pramlintide plus metreleptin, buprorion plus naltrexone (Contrave), phentermine plus topiramate (Qsymia).

In some embodiments, the anti-obesity agents used in combination with compounds of the invention are selected from gut-selective MTP inhibitors (e.g. dirlotapide, mitratapide, implitapide, R56918), CCK-A agonists, 5-HT2C agonists (e.g. lorcaserin/Belviq), MCR4 agonists, lipase inhibitors (e.g. Cetilistat), PYY3-36 (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, the compounds and compositions, according to the method of the present invention, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et al. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, the compounds and compositions, according to the method of the present invention, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" Biochem Biophys Res Commun. (2009) 385(3), 302-306; Chajes et al. "Acetyl-CoA Carboxylase alpha Is Essential to Breast Cancer Cell Survival" Cancer Res. (2006) 66, 5287-5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, the compounds and compositions, according to the method of the present invention, may be administered using any amount and any route of administration effective for treating or lessening the severity of a melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

Compounds of the present invention find special utility in triple negative breast cancer, as the tumor suppressor protein BRCA1 binds and stabilizes the inactive form of ACC, thus upregulating de novo lipid synthesis, resulting in cancer cell proliferation Brunet et al. "BRCA1 and acetyl-CoA carboxylase: the metabolic syndrome of breast cancer" Mol. Carcinog. (2008) 47(2), 157-163.

In some embodiments, the compounds and compositions, according to the method of the present invention, may be administered using any amount and any route of administration effective for treating or lessening the severity of a liposarcoma. Liposarcomas have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, the compounds and compositions, according to the method of the present invention, may be administered using any amount and any route of administration effective for treating or lessening the severity of a liver disease. In some embodiments, the liver disease is selected from hepatitis C, hepatocellular carcinoma, familial combined hyperlipidemia and non-alcoholic steatohepatitis (NASH), liver cancer, cholangiocarcinoma, angiosarcoma, hemangiosarcoma, and progressive familial intrahepatic cholestasis.

In some embodiments, the compounds and compositions, according to the method of the present invention, may be administered using any amount and any route of administration effective for treating or lessening the severity of a bacterial infection or inhibiting the growth of bacteria.

In some embodiments, the compounds and compositions, according to the method of the present invention, may be administered using any amount and any route of administration effective for treating or lessening the severity of a fungal infection or inhibiting the growth of fungal cells (Shen et al. "A Mechanism for the Potent Inhibition of Eukaryotic Acetyl-Coenzyme A Carboxylase by Soraphen A, a Macrocyclic Polyketide Natural Product" Molecular Cell (2004) 16, 881-891).

In some embodiments, the compounds and compositions, according to the method of the present invention, may be administered using any amount and any route of administration effective for treating or lessening the severity of a bacterial infection (Tong, L. et al. J. Cell. Biochem. (2006) 99, 1476-1488).

In some embodiments, the compounds and compositions, according to the method of the present invention, may be administered using any amount and any route of administration effective for treating or lessening the severity of a viral infection (Munger et al. Nat. Biotechnol. (2008) 26, 1179-1186). In some embodiments, the viral infection is Hepatitis C.

In some embodiments, the compounds and compositions, according to the method of the present invention, may be administered using any amount and any route of administration effective for treating or lessening the severity of a neurological disease (Henderson et al. Neurotherapeutics (2008) 5, 470-480; Costantini et al. Neurosci. (2008) 9 Suppl. 2:S16; Baranano et al. Curr. Treat. Opin. Neurol. (2008) 10, 410-419).

In some embodiments, the compounds and compositions, according to the method of the present invention, may be administered using any amount and any route of administration effective for treating or lessening the severity of a parasitic infection or inhibiting the growth of parasites (e.g. malaria and toxoplasma: Gornicki et al. "Apicoplast fatty acid biosynthesis as a target for medical intervention in apicomplexan parasites" International Journal of Parasitology (2003) 33, 885-896; Zuther et al. "Growth of *Toxoplasma gondii* is inhibited by aryloxyphenoxypropionate herbicides targeting acetyl-CoA carboxylase" PNAS (1999) 96 (23) 13387-13392).

In some embodiments, the compounds and compositions, according to the method of the present invention, may be administered using any amount and any route of administration effective for treating or lessening the severity of a cardiac disorder. In some embodiments, the cardiac disorder is cardiac hypertrophy. In some embodiments the cardiac disorder is treated or its severity lessened by the cardioprotective mechanism resulting from increased fatty acid oxidation via ACC inhibition (Kolwicz et al. "Cardiac-specific deletion of acetyl CoA carboxylase 2 (ACC2) prevents metabolic remodeling during pressure-overload hypertrophy" Circ. Res. (2012); DOI: 10.1161/CIRCRESAHA.112.268128).

In certain embodiments, the compounds and compositions, according to the method of the present invention, may be used as herbicides. In some embodiments, the present invention provides a method to inhibit the growth or viability of plants comprising treating plants with compounds of the present invention. In some embodiments of the present invention, compounds of the present invention can be used to inhibit the growth or viability of plants by inhibiting ACC. In some embodiments, the method of the present invention comprises using compounds of the present invention to inhibit fatty acid production in or increase fatty acid oxidation in plants.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Another embodiment of the present invention relates to a method of inhibiting ACC in a patient comprising the step of administering to said patient a compound of the present invention, or a composition comprising said compound.

According to another embodiment, the invention relates to a method of inhibiting fatty acid production, stimulating fatty acid oxidation, or both, in a patient comprising the step of administering to said patient a compound of the present invention, or a composition comprising said compound. According to certain embodiments, the invention relates to a method of inhibiting fatty acid production, stimulating fatty acid oxidation, or both in a patient, leading to decreasing obesity or alleviating symptoms of metabolic syndrome, comprising the step of administering to said patient a compound of the present invention, or a composition comprising said compound. In other embodiments, the present invention provides a method for treating a disorder mediated by ACC, in a patient in need thereof, comprising the step of administering to said patient a compound according to the present invention or pharmaceutically acceptable composition thereof. Such disorders are described in detail herein.

In some embodiments the compounds and compositions of the present invention may be used in a method of treating obesity or another metabolic disorder. In certain embodiments the compounds and compositions of the present invention may be used to treat obesity or other metabolic disorder in a mammal. In certain embodiments the mammal is a human patient. In certain embodiments the compounds and compositions of the present invention may be used to treat obesity or other metabolic disorder in a human patient.

In some embodiments the present invention provides a method of treating obesity or another metabolic disorder, comprising administering a compound or composition of the present invention to a patient with obesity or another metabolic disorder. In certain embodiments the method of treating obesity or another metabolic disorder comprises administering compounds and compositions of the present invention to a mammal. In certain embodiments the mammal is a human. In some embodiments the metabolic disorder is dyslipidemia or hyperlipidemia. In some embodiments, the obesity is a symptom of Prader-Willi syndrome, Bardet-Biedl syndrome, Cohen syndrome or MOMO syndrome. In some embodiments, the obesity is a side effect of the administration of another medication, including but not limited to insulin, sulfunylureas, thiazolidinediones, antipsychotics, antidepressants, steroids, anticonvulsants (including phenyloin and valproate), pizotifen, or hormonal contraceptives.

In certain embodiments, the present invention provides a method of treating cancer or another proliferative disorder, comprising administering a compound or composition of the present invention to a patient with cancer or another proliferative disorder. In certain embodiments, the method of treating cancer or another proliferative disorder comprises administering compounds and compositions of the present invention to a mammal. In certain embodiments, the mammal is a human.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the compounds and compositions described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by compounds or compositions of the invention is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL). In certain preferred embodiments the cancer to be treated by compounds or compositions of the invention is one bearing an activated MAPK pathway. In some embodiments the cancer bearing an activated MAPK pathway is a melanoma. In certain preferred embodiments the cancer treated by compounds or compositions of the invention is one associated with BRCA1 mutation. In an especially preferred embodiment, the cancer treated by compounds or compositions of the invention is a triple negative breast cancer.

In certain embodiments, the disease which can be treated by compounds of the invention are neurological disorders. In some embodiments, the neurological disorder is Alzheimer's Disease, Parkinson's Disease, epilepsy, ischemia, Age Associated Memory Impairment, Mild Cognitive Impairment, Friedreich's Ataxia, GLUT1-deficient epilepsy, Leprechaunism, Rabson-Mendenhall Syndrome, Coronary Arterial Bypass Graft dementia, anaesthesia-induced memory loss, amyotrophic lateral sclerosis, gliomaor Huntington's Disease.

In certain embodiments, the disease which can be treated by compounds of the invention is an infectious disease. In some embodiments, the infectious disease is a viral infection. In some embodiments the viral infection is cytomegalovirus infection or influenza infection. In some embodiments, the infectious disease is a fungal infection. In some embodiments, the infectious disease is a bacterial infection.

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated".

In certain embodiments, a provided compound, or composition thereof, is administered in combination with another inhibitor of ACC or antiobesity agent. In some embodiments, a provided compound, or composition thereof, is administered in combination with one or more other therapeutic agents. Such therapeutic agents agents include, but are not limited to agents such as orlistat (Xenical), CNS stimulants, Qsymia, or Belviq.

In certain embodiments, a provided compound, or a composition thereof, is administered in combination with another anti-cancer, cytotoxin, or chemotherapeutic agent, to a patient in need thereof.

In certain embodiments, the anti-cancer or chemotherapeutic agents used in combination with compounds or compositions of the invention include, but are not limited to metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall$^T$M, Trisenox®, TSPA, TYKERB®, VCR, Vectibix™, Velban®, Velcade®, VePesid®, Vesanoid®, Viadur™, Vidaza®, Vinblastine, Vinblastine Sulfate, VincasarPfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, compounds of the present invention may be administered together with a biguanide selected from metformin, phenformin, or buformin, to a patient in need thereof. In certain embodiments, the patient administered a combination of a compound of the invention and a biguanide is suffering from a cancer, obesity, a liver disease, diabetes or two or more of the above.

In certain embodiments, a combination of 2 or more therapeutic agents may be administered together with compounds of the invention. In certain embodiments, a combination of 3 or more therapeutic agents may be administered with compounds of the invention.

Other examples of agents the inhibitors of this invention may also be combined with include, without limitation: vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, AMPK activators, PCSK9 inhibitors, SREBP site 1 protease inhibitors, HMG CoA-reductase inhibitors, antiemetics (e.g. 5-HT3 receptor antagonists, dopamine antagonists, NK1 receptor antagonists, histamine receptor antagonists, cannabinoids, benzodiazepines, or a nticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, compounds of the present invention, or a pharmaceutically acceptable composition thereof, are administered in combination with antisense agents, a monoclonal or polyclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 g/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

What is claimed is:
1. A compound of Formula (I) or a pharmaceutically acceptable salt of an enantiomer thereof,

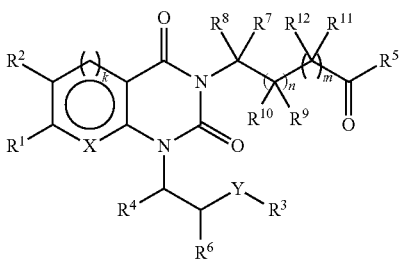

wherein
each of m, n, and k independently is 0, 1, or 2;
R¹ is H, halo, alkyl, haloalkyl, CN, amido, aryl, or heteroaryl,
R² is H, alkyl, haloalkyl, CN, hydroxyl, or alkoxy;
R³ is H, alkyl, aryl, heteroaryl, cycloalkyl, or heterocycloalkyl, and is optionally substituted with halo, alkyl, or haloalkyl;
R⁴ is H, alkyl, haloalkyl, CN, hydroxyl, or alkoxy;
R⁵ is OR N(R)₂;
R⁶ is aryl or heteroaryl and is optionally substituted with halo, alkyl, haloalkyl, CN, hydroxyl, or alkoxy;
R⁷ and R⁸, together with the carbon atom to which they are bonded, form a 3- to 6-membered cycloalkyl which optionally contains one or two ring hetero groups each independently being 0 or NR'; and R⁹ is H, alkyl, haloalkyl, alkoxy, or haloalkoxy;
or alternatively, R⁹ and R⁸, together with the carbon atoms to which they are bonded, form a 3- to 7-membered cycloalkyl which optionally contains one or two ring hetero groups each independently being 0 or NR'; and R⁷ is H, alkyl, haloalkyl, alkoxy, or haloalkoxy;
R¹⁰, R¹¹, and R¹² independently, is H, alkyl, haloalkyl, alkoxy, or haloalkoxy;
X is C(R)₂, S, O, or NR';
Y is S, O, or NR';
each R independently is H, alkyl, halo, or haloalkyl; and
each of R' independently is H, halo, alkyl, haloalkyl, CN, or hydroxyl.

2. The compound of claim 1, wherein k is 0.
3. The compound of claim 1, wherein X is S or O.
4. The compound of claim 3, wherein X is S.
5. The compound of claim 1, wherein k is 1.
6. The compound of claim 1, wherein X is CH₂, S, O, or NH.
7. The compound of claim 6, wherein X is CH₂.
8. The compound of claim 1, wherein Y is S, O or NH.
9. The compound of claim 8, wherein Y is O.
10. The compound of claim 1, wherein R¹ is halo, haloalkyl, CN, or heteraryl.
11. The compound of claim 10, wherein R¹ is Br, F, CF₃, CN, oxazolyl, oxazolyl, or oxadiazolyl.
12. The compound of claim 11, wherein R¹ is Br, F, CF₃, CN, 2-oxazolyl, 4-oxazolyl, or 4-oxadiazolyl, or 5-oxadiazolyl.
13. The compound of claim 1, wherein each of R² and R⁴ independently is H or alkyl.
14. The compound of claim 1, wherein R³ is cycloalkyl or heterocycloalkyl and is optionally substituted with halo, alkyl, or haloalkyl.
15. The compound of claim 14, wherein R³ is heterocycloalkyl optionally substituted with halo, alkyl, or haloalkyl.

16. The compound of claim 15, wherein R³ is tetrahydro-2H-pyranyl, tetrahydrofuranyl, tetrahydro-2H-thiopyranyl, or tetrahydrothiophenyl and is optionally substituted with halo, alkyl, or haloalkyl.
17. The compound of claim 16, wherein R³ is 4-(tetrahydro-2H-pyranyl) or 3-(tetrahydrofuranyl).
18. The compound of claim 1, wherein R⁵ is OR N(R)₂, wherein each R is independently H or alkyl.
19. The compound of claim 18, wherein R is H.
20. The compound of claim 1, wherein R⁶ is phenyl, pyridinyl, pyrrolyl, or thiophenyl, and is optionally substituted with halo, alkyl, haloalkyl, CN, hydroxyl, or alkoxy.
21. The compound of claim 20, wherein R⁶ is phenyl substituted with halo, alkyl, haloalkyl, or alkoxy.
22. The compound of claim 1, wherein m is 0 and n is 1.
23. The compound of claim 1, wherein R⁷ and R⁸, together with the carbon atom to which they are bonded, form a 3- to 6-membered cycloalkyl which optionally contains one ring hetero group of O.
24. The compound of claim 23, wherein R⁷ and R⁸, together with the carbon atom to which they are bonded, form a 3- to 6-membered cycloalkyl which is

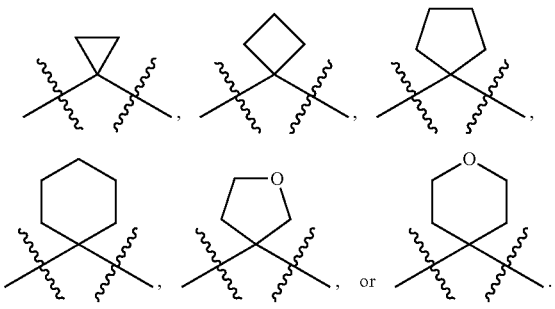

25. The compound of claim 1, wherein R⁸ and R⁹, together with the carbon atoms to which they are bonded, form a 3- to 7-membered cycloalkyk; and R⁷ and R¹⁰, independently, is H, alkyl, or haloalkyl.
26. The compound of claim 1, wherein each R and each R' independently is H, halo, alkyl, or haloalkyl.
27. A compound or a pharmaceutically acceptable salt of an enantiomer thereof, wherein the compound is selected from the group consisting of:

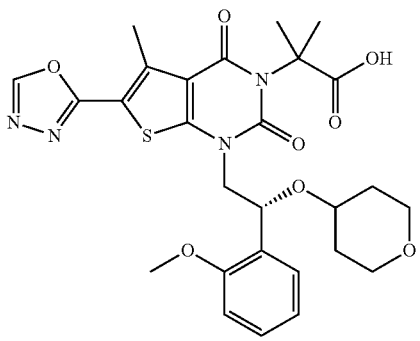

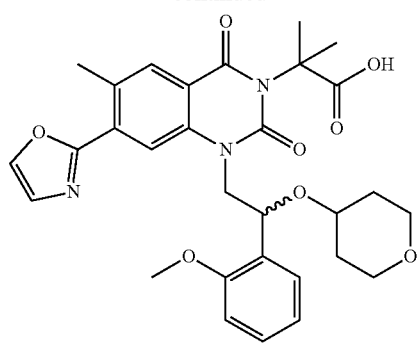
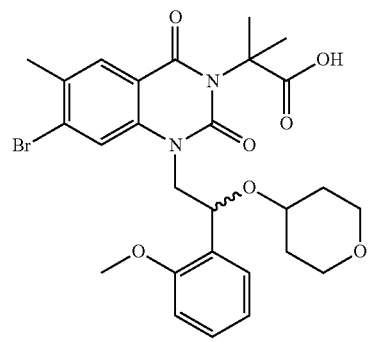
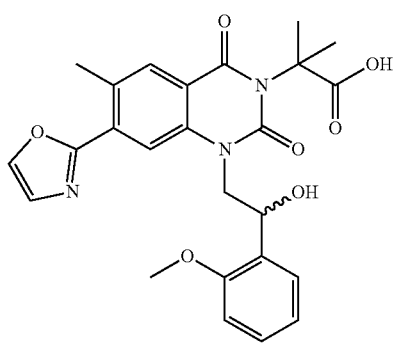
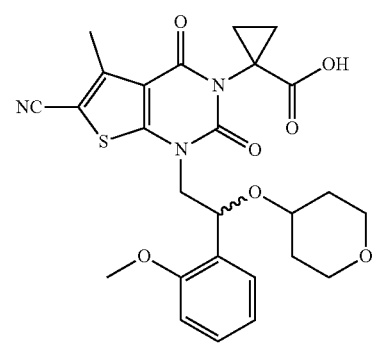
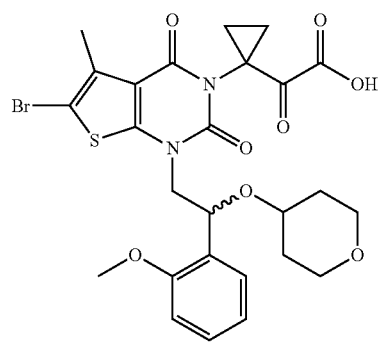
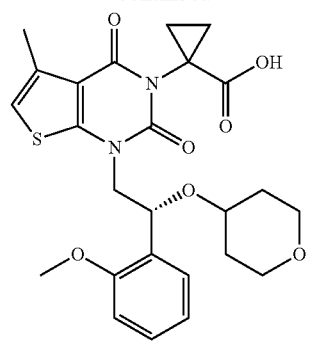
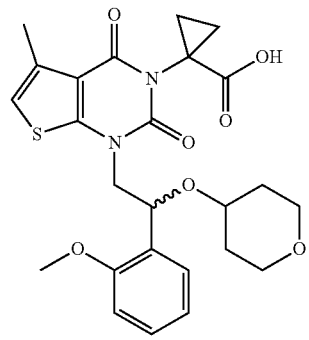
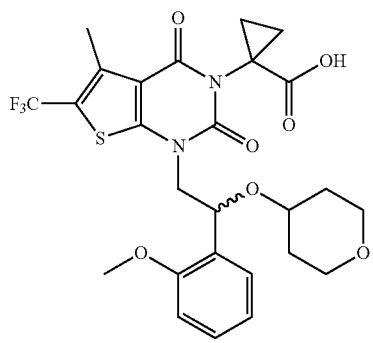
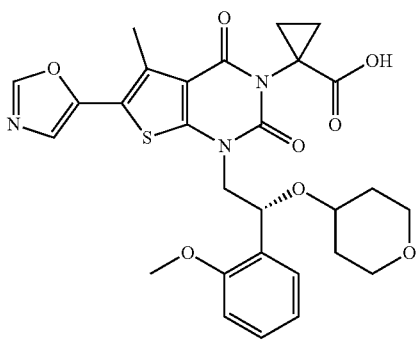
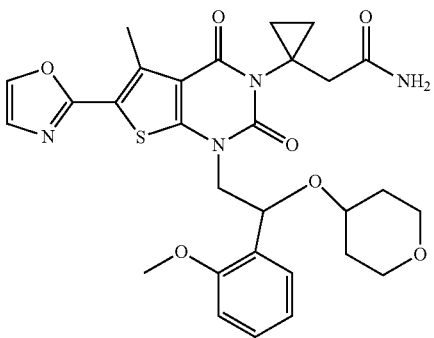

87
-continued
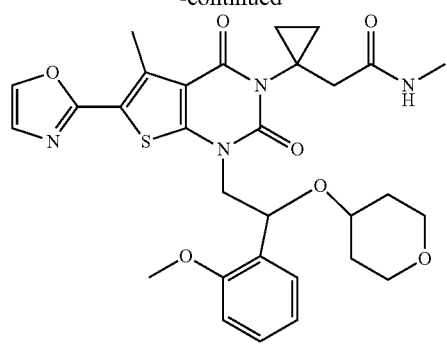
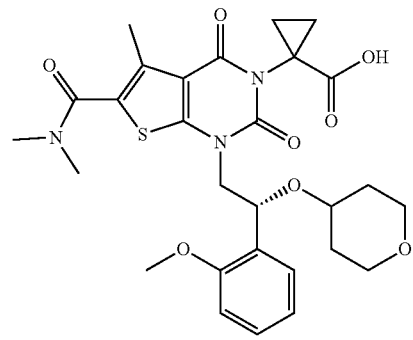
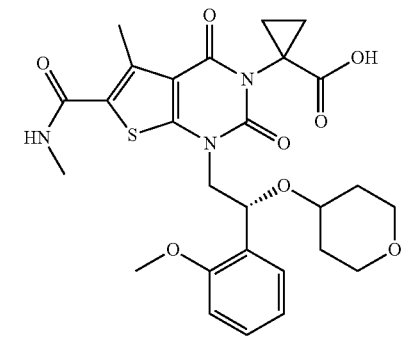
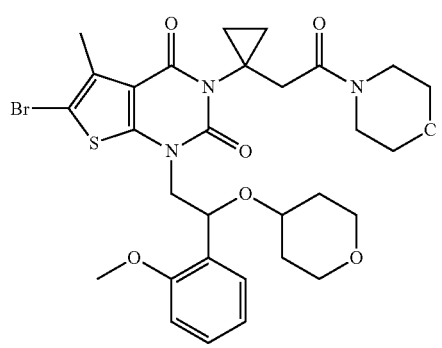
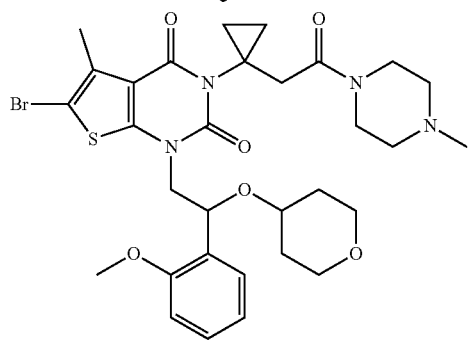
88
-continued
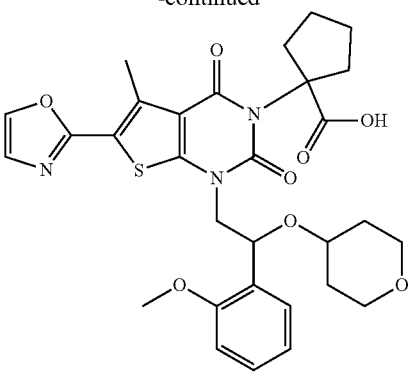
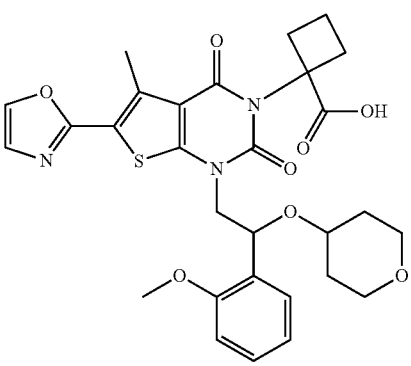
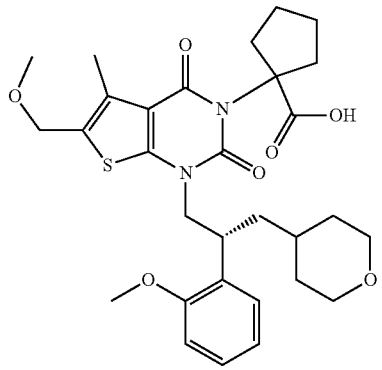
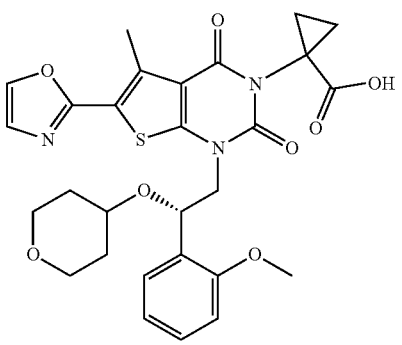

89
-continued
90
-continued
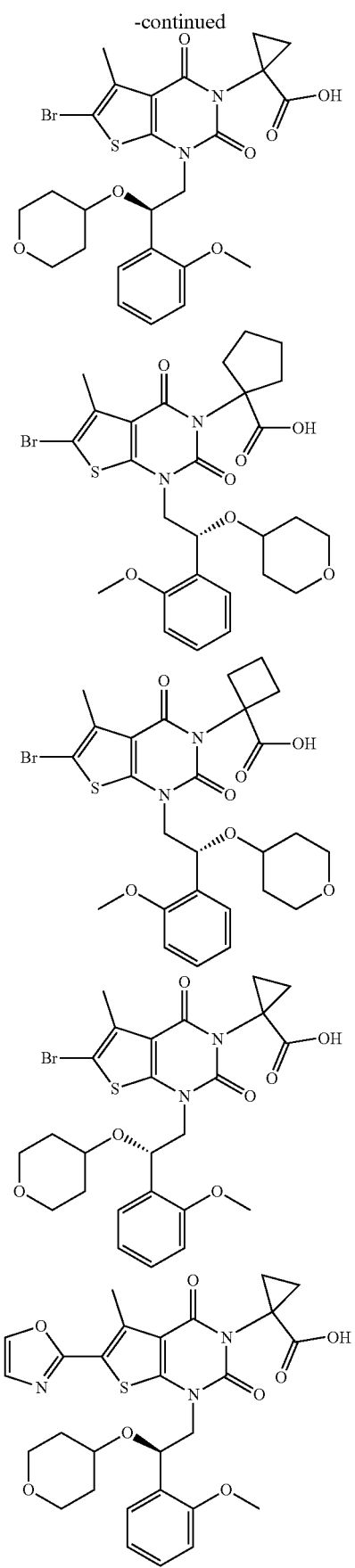
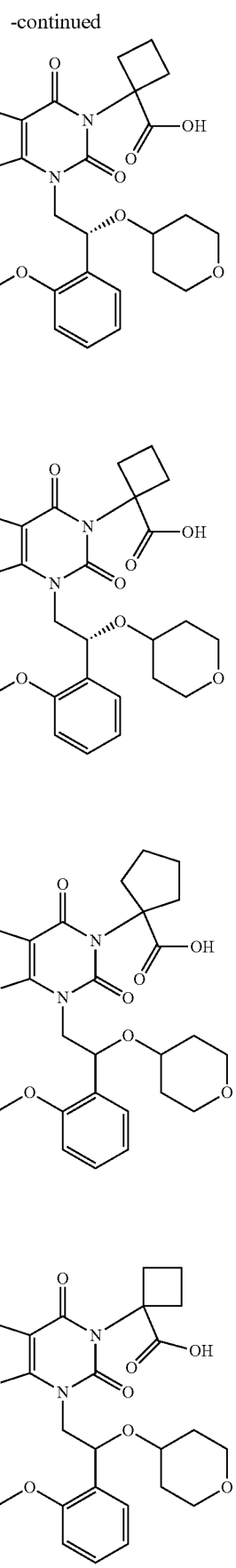

-continued
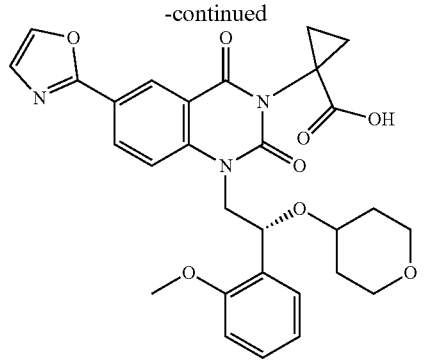
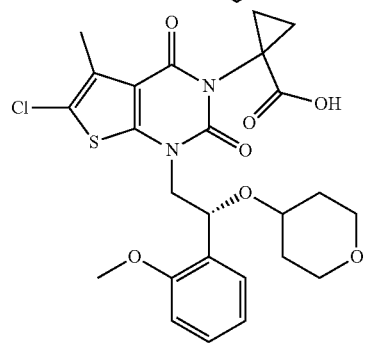
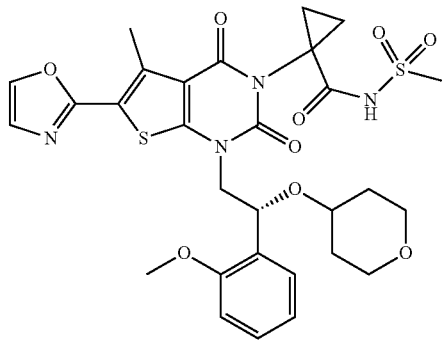
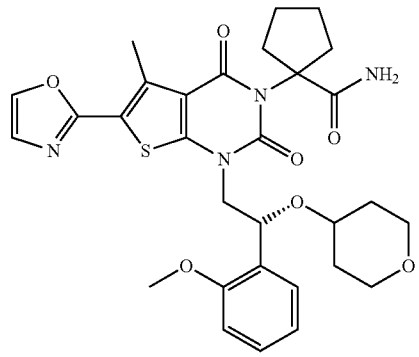
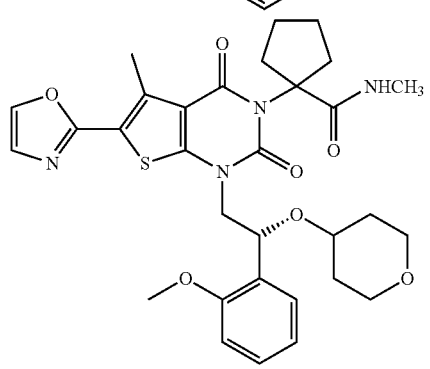
-continued
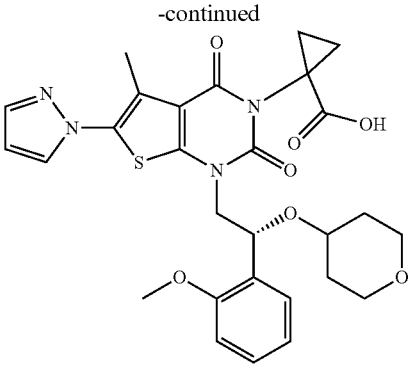
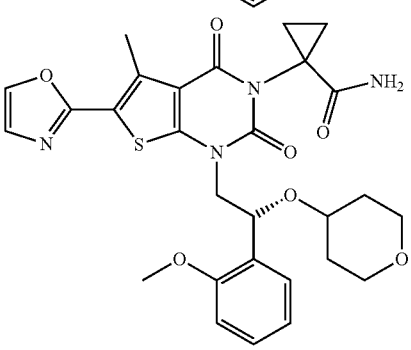
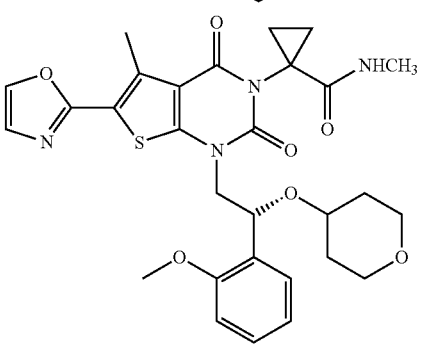
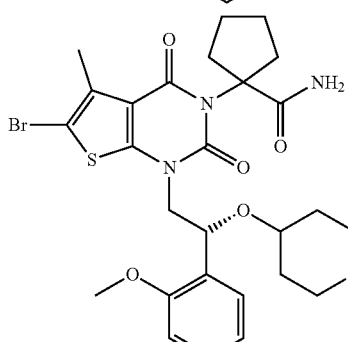
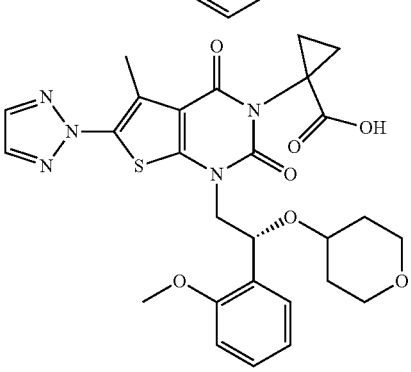

93
-continued
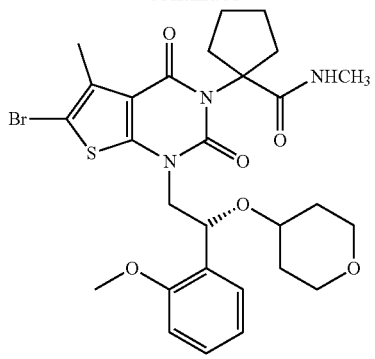
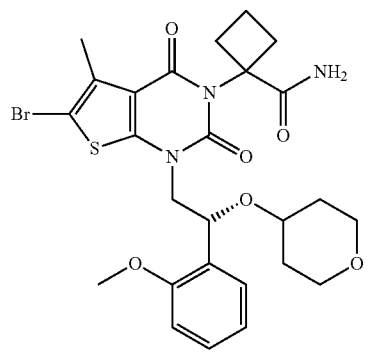
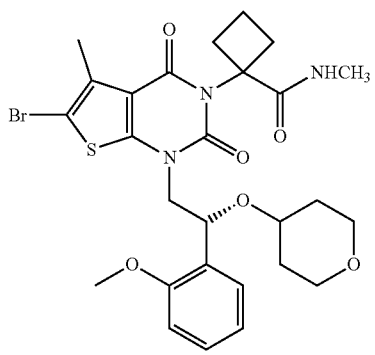
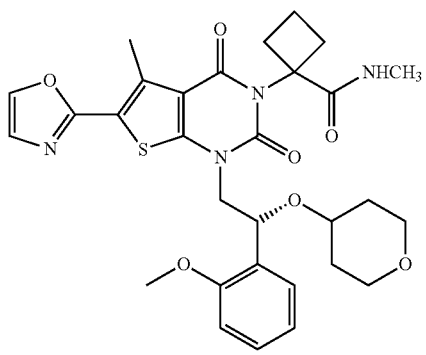
94
-continued
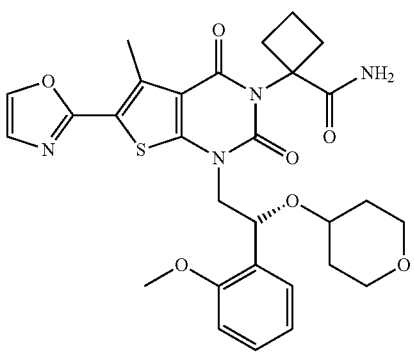
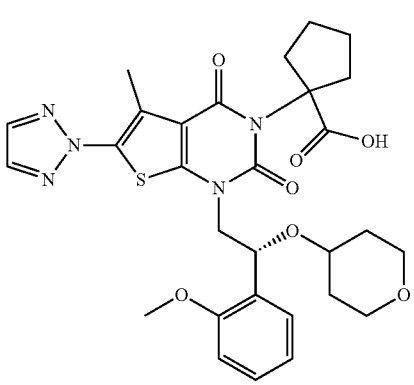
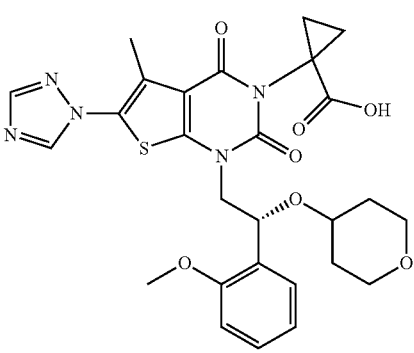
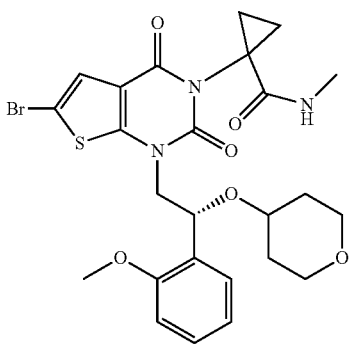

95
-continued
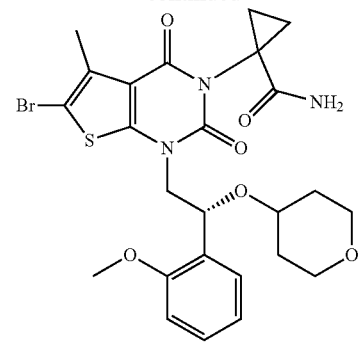
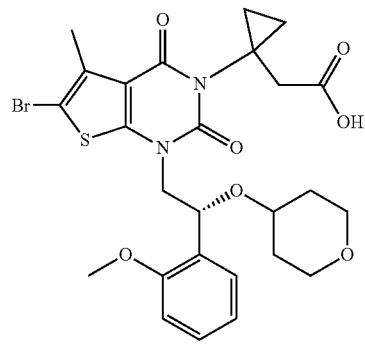
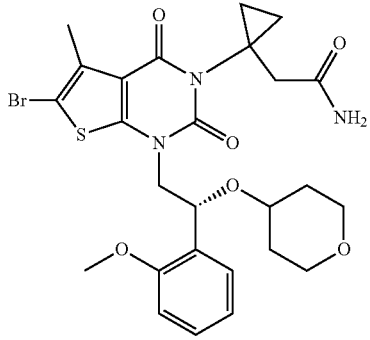
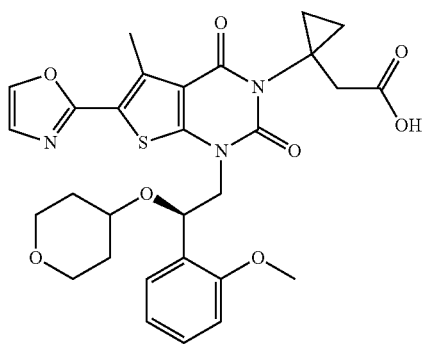
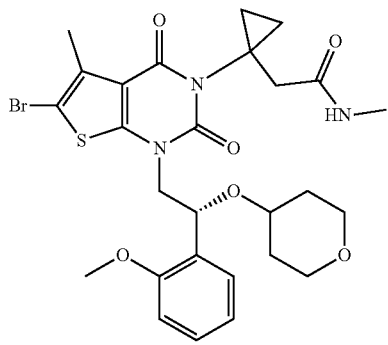
96
-continued
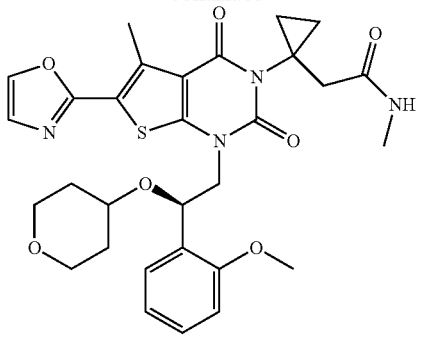
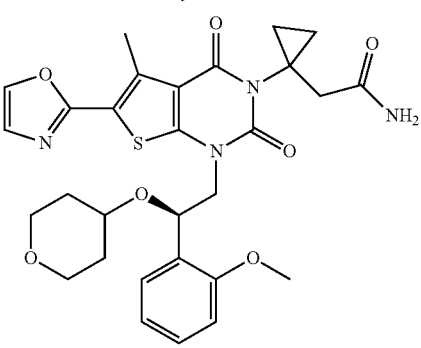
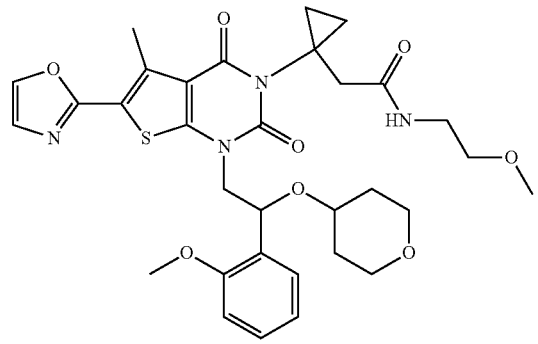
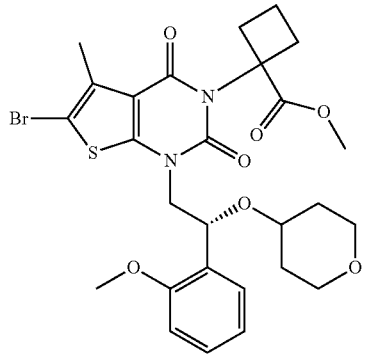
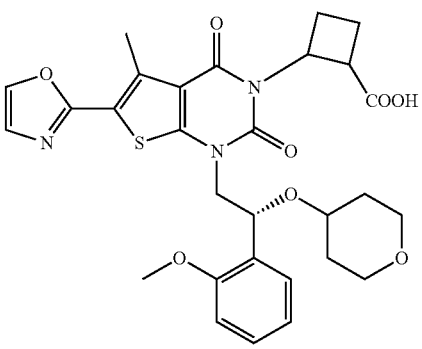

97
-continued
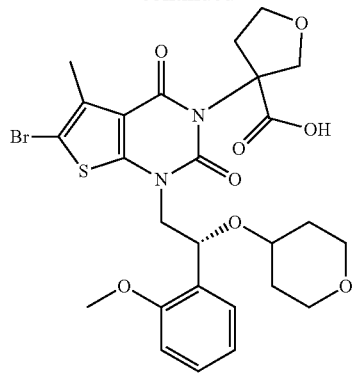
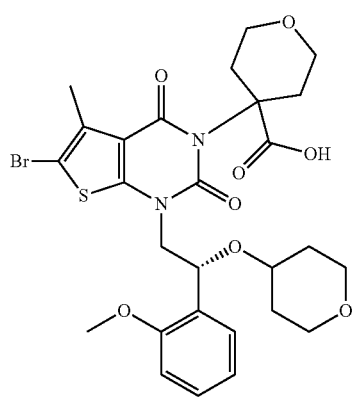
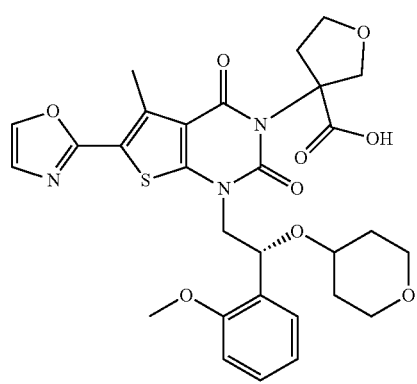
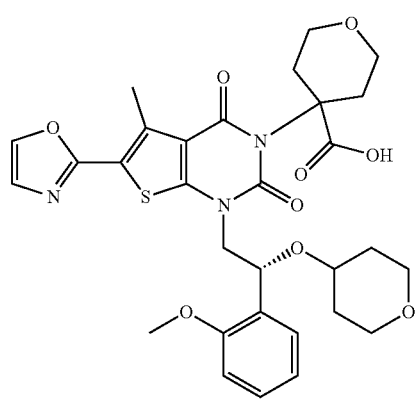
98
-continued
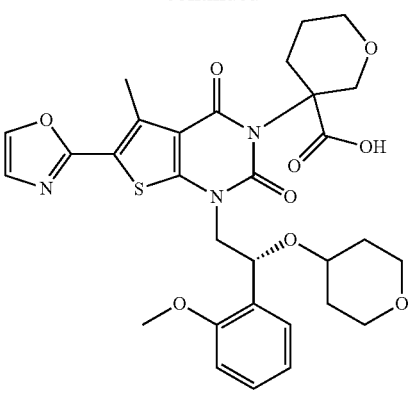
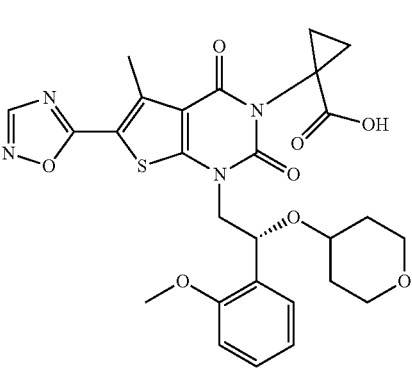
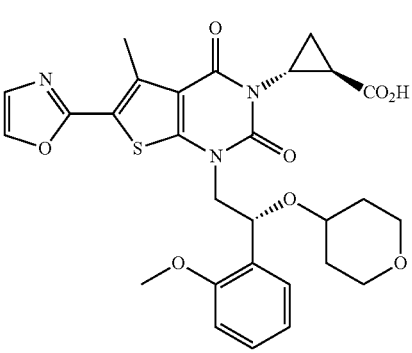
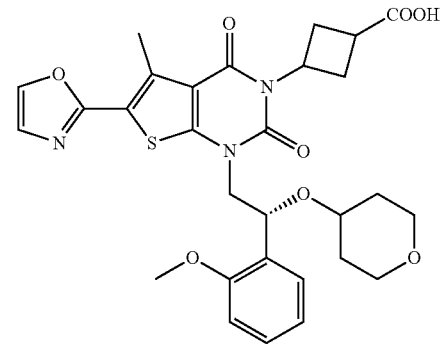

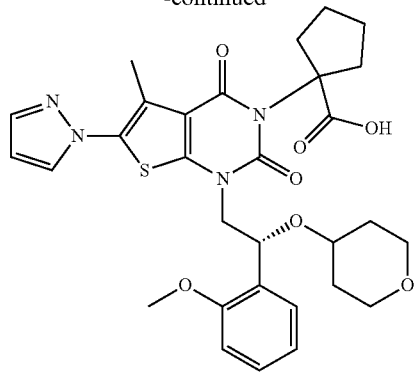
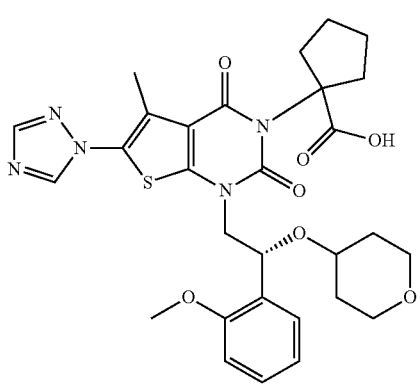
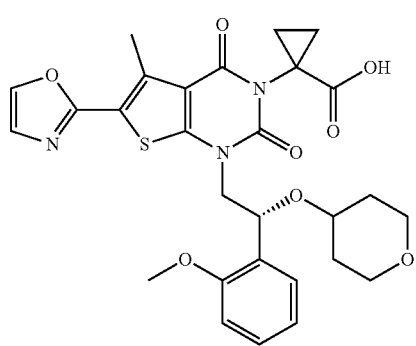
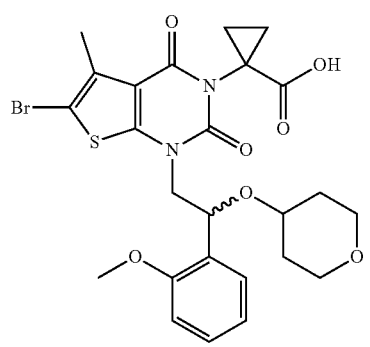
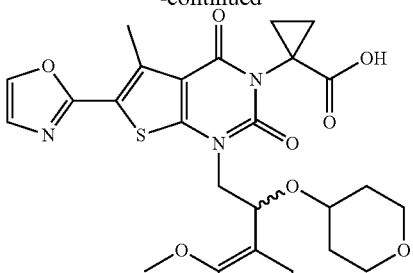
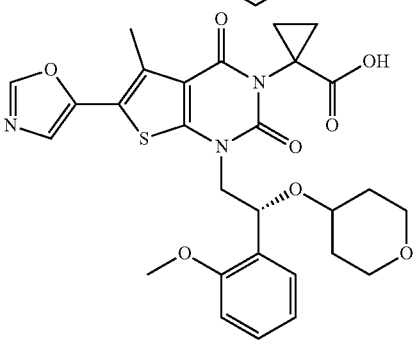
and
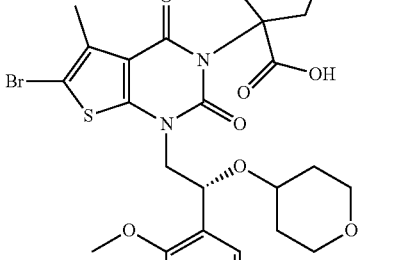
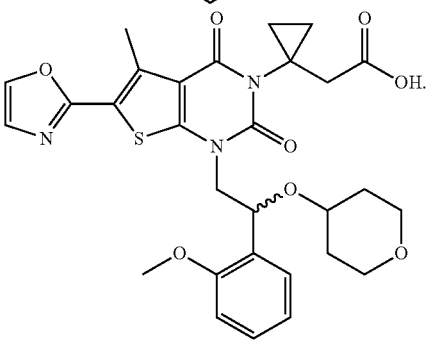
28. A pharmaceutical composition comprising a therapeutically effective amount of a compound of claim 1 and a pharmaceutically acceptable carrier.
29. A pharmaceutical composition comprising a therapeutically effective amount of a compound of claim 27 and a pharmaceutically acceptable carrier.
* * * * *